United States Patent [19]

Humbert et al.

[11] 4,281,012
[45] Jul. 28, 1981

[54] [4H]-1,3-BENZODIOXIN-2-CARBOXYLIC ACIDS

[75] Inventors: Daniel Humbert, Fontenay-sous-Bois; François Clémence, Paris; Michele Dagnaux, Fontenay-sous-Bois, all of France

[73] Assignee: Roussel Uclaf, Paris, France

[21] Appl. No.: 34,432

[22] Filed: Apr. 30, 1979

[30] Foreign Application Priority Data

May 3, 1978 [FR] France ................... 78 13095
May 3, 1978 [FR] France ................... 78 13096

[51] Int. Cl.³ ............... A61K 31/335; C07D 319/08
[52] U.S. Cl. ..................... 424/278; 260/340.3
[58] Field of Search .......... 260/340.9 R, 340.3; 424/278

[56] References Cited

U.S. PATENT DOCUMENTS

| | | | |
|---|---|---|---|
| 3,835,159 | 9/1974 | Najer et al. | 260/340.3 |
| 3,836,543 | 9/1974 | Grisar | 260/340.3 |
| 4,046,762 | 9/1977 | Manghisi et al. | 260/340.3 X |
| 4,056,540 | 11/1977 | Buchanan et al. | 260/340.3 |

FOREIGN PATENT DOCUMENTS

| | | |
|---|---|---|
| 2508826 | 9/1976 | Fed. Rep. of Germany . |
| 2508826 | 9/1976 | Fed. Rep. of Germany . |
| 1312893 | 11/1962 | France ................... 260/340.3 |

Primary Examiner—Ethel G. Love
Attorney, Agent, or Firm—Hammond & Littell, Weissenberger and Muserlian

[57] ABSTRACT

Novel racemates and optically active isomers and mixtures of isomers of [4H]-1,3-benzodioxin-2-carboxylic acid compounds of the formula

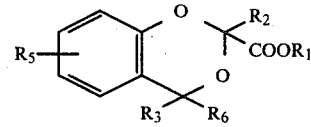

wherein $R_1$ is selected from the group consisting of hydrogen, alkyl of 1 to 5 carbon atoms, dialkylamino alkyl with alkyls of 1 to 5 carbon atoms, alkali metal, alkaline earth metal, aluminum, —$NH_4$, non-toxic pharmaceutically acceptable amines, 2,3-dihydroxypropanyl and (2,2-dimethyl-1,3-dioxolan-4-yl)-methyl, $R_2$ is selected from the group consisting of hydrogen and alkyl of 1 to 5 carbon atoms, $R_3$ and $R_6$ are individually selected from the group consisting of hydrogen, alkyl of 1 to 6 carbon atoms, ethenyl and cyclohexyl and taken together with the carbon atom to which they are attached form cyclohexyl, $R_5$ is selected from the group consisting of hydrogen and halogen or $R_1$ and $R_2$ have the above definitions, $R_6$ is

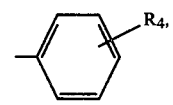

$R_4$ and $R_5$ are individually selected from the group consisting of hydrogen, halogen, —$CF_3$, cyclohexyl, alkoxy of 1 to 3 carbon atoms, alkyl of 1 to 3 carbon atoms and p-chlorophenoxy and $R_3$ is selected from the group consisting of 2-propenyl, ethenyl, cyclohexyl, benzyl, hydrogen and alkyl of 1 to 5 carbon atoms with the proviso that when $R_3$ is alkyl, at least one of $R_4$ and $R_5$ is no hydrogen or halogen and when $R_3$ is hydrogen, at least one of $R_4$ and $R_5$ is not hydrogen, halogen or —$CF_3$ and the non-toxic, pharmaceutically acceptable acid addition salts thereof when $R_1$ is dialkylaminoalkyl which have a marked hypolipemiant activity and reduces the plasmatic level of lipids, triglycerides and cholestrol and their preparation.

15 Claims, No Drawings

[4H]-1,3-BENZODIOXIN-2-CARBOXYLIC ACIDS

STATE OF THE ART

U.S. Pat. No. 4,056,540 and copending commonly assigned U.S. Pat. application Ser. No. 847,776 filed Nov. 2, 1977 describe 1,3-benzodioxin compounds.

OBJECTS OF THE INVENTION

It is an object of the invention to provide the novel 1,3-benzodioxin-2-carboxylic acid compounds of formula I and to provide a novel process and novel intermediates therefore.

It is another object of the invention to provide novel hypolipemiant compositions and a novel method of inducing hypolipemic activity in warm-blooded animals.

These and other objects and advantages of the invention will become obvious from the following detailed description.

THE INVENTION

The novel compounds of the invention are selected from the group consisting of racemates and optically active isomers and mixtures of isomers of [4H]-1,3-benzodioxin-2-carboxylic acid compounds of the formula

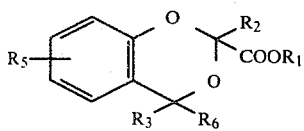

wherein $R_1$ is selected from the group consisting of hydrogen, alkyl of 1 to 5 carbon atoms, dialkylamino alkyl with alkyls of 1 to 5 carbon atoms, alkali metal, alkaline earth metal, aluminum, $-NH_4$, non-toxic, pharmaceutically acceptable amines, 2,3-dihydroxypropanyl and (2,2-dimethyl-1,3-dioxolan-4-yl)-methyl, $R_2$ is selected from the group consisting of hydrogen and alkyl of 1 to 5 carbon atoms, $R_3$ and $R_6$ are individually selected from the group consisting of hydrogen, alkyl of 1 to 6 carbon atoms, ethenyl and cyclohexyl and taken together with the carbon atoms to which they are attached form cyclohexyl, $R_5$ is selected from the group consisting of hydrogen and halogen or $R_1$ and $R_2$ have the above definitions, $R_6$ is

$R_4$ and $R_5$ are individually selected from the group consisting of hydrogen, halogen, $-CF_3$, cyclohexyl, alkoxy of 1 to 3 carbon atoms, alkyl of 1 to 3 carbon atoms and p-chlorophenoxy and $R_3$ is selected from the group consisting of 2-propenyl, ethenyl, cyclohexyl, benzyl, hydrogen and alkyl of 1 to 5 carbon atoms with the proviso that when $R_3$ is alkyl, at least one of $R_4$ and $R_5$ is not hydrogen or halogen and when $R_3$ is hydrogen, at least one of $R_4$ and $R_5$ is not hydrogen, halogen or $-CF_3$ and the non-toxic, pharmaceutically acceptable acid addition salts thereof when $R_1$ is dialkylaminoalkyl.

Especially preferred compounds of the invention are racemates, optically active isomers and mixtures thereof of those of the formula

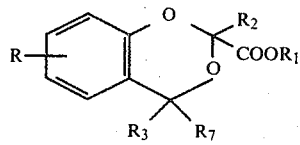

wherein $R_1$ and $R_2$ have the above definitions, $R_5$ is selected from the group consisting of hydrogen and halogen, $R_3$ and $R_7$ are individually selected from the group consisting of hydrogen, alkyl of 1 to 5 carbon atoms, ethenyl and cyclohexyl or $R_3$ and $R_7$ taken together with the carbon atom they are attached form cyclohexyl and non-toxic, pharmaceutically acceptable acid addition salts thereof when $R_1$ is dialkylaminoalkyl and racemates, optically active isomers and mixtures thereof of those having the formula

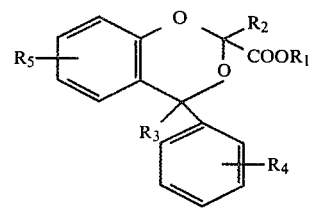

wherein $R_1$ and $R_2$ are individually selected from the group consisting of hydrogen, alkyl of 1 to 5 carbon atoms, alkali metal, ammonium, alkaline earth metal, aluminum and non-toxic, pharmaceutically acceptable amines, $R_4$ and $R_5$ are individually selected from the group consisting of hydrogen, halogen, $-CF_3$, cyclohexyl, alkoxy of 1 to 3 carbon atoms, alkyl of 1 to 3 carbon atoms and p-chlorophenoxy and $R_3$ is selected from the group consisting of 2-propenyl, ethenyl, cyclohexyl, benzyl, alkyl of 1 to 5 carbon atoms and hydrogen with the proviso that when $R_3$ is alkyl, at least one of $R_4$ and $R_5$ is not hydrogen or halogen and when $R_3$ is hydrogen, at least one of $R_4$ and $R_5$ is not hydrogen, halogen or $-CF_3$.

Examples of suitable alkyl groups are methyl, ethyl, propyl, isopropyl, n-butyl, isobutyl, tert.-butyl, pentyl or hexyl. Examples of suitable alkoxy groups of 1 to 3 carbon atoms are methoxy, ethoxy, propoxy and isopropoxy. Examples of suitable halogens are chlorine, bromine and fluorine.

Examples of suitable salts of formula I are alkali metal salts such as sodium, potassium or lithium, alkaline earth metal salts such as calcium, aluminum, $-NH_4$ and suitable amines such as monoalkylamines like methylamine, ethylamine, propylamine, dialkylamines like dimethylamine, diethylamine, di-n-propylamine, trialkylamines like triethylamine and heterocyclics like piperidine, morpholine, piperazine and pyrrolidine.

Examples of suitable acids for the non-toxic, pharmaceutically acceptable acid addition salts are inorganic acids such as hydrochloric acid, hydrobromic acid, hydroiodic acid, nitric acid, sulfuric acid and phosphoric acid and organic acids such as acetic acid, maleic acid, fumaric acid, succinic acid, tartaric acid, alkylmono and disulfonic acids such as methane sulfonic acid, ethane sulfonic acid, propane sulfonic acid and α,β-ethane disulfonic acid.

The compounds of formula I may exist in the form of racemates, optically active isomers and mixtures of isomers and the latter term is intended to include mixtures of racemic isomers or mixtures of optically active isomers in any proportion. It includes mixtures of any proportion of racemics, mixtures of any proportion of 2 optical antipodes and mixtures of any proportion of optically active diastereo isomers.

Examples of specific preferred compounds of the invention are the compounds of formula $I_A$ wherein $R_3$ and $R_7$ are identical, those wherein $R_3$ and $R_7$ are identical and are either hydrogen or alkyl of 1 to 5 carbon atoms, the compounds of formula $I_B$ wherein $R_1$ and $R_2$ are individually hydrogen or methyl, $R_4$ and $R_5$ are individually hydrogen, chlorine, —$CF_3$, cyclohexyl, methoxy, methyl or p-chlorophenoxy and $R_3$ is 2-propenyl, ethenyl, cyclohexyl, methyl or benzyl with the proviso that when $R_3$ is methyl, at least one of $R_4$ and $R_5$ is not hydrogen or chlorine and the compounds of formula $I_B$ wherein $R_1$ and $R_2$ are individually hydrogen or methyl, $R_4$ is hydrogen or —$CF_3$, $R_5$ is hydrogen, chlorine, —$CF_3$, cyclohexyl, methoxy or p-chlorophenoxy and $R_3$ is 2-propenyl, ethenyl, cyclohexyl, benzyl and methyl with the proviso that when $R_3$ is methyl, at least one of $R_4$ and $R_5$ is not hydrogen or chlorine and their salts.

Especially preferred compounds are racemates and optically active isomers of methyl 6-chloro-4-methyl-4-(3-trifluoromethylphenyl)-[4H]-1,3-benzodioxin-2-carboxylate and methyl 6-methoxy-4-methyl-4-phenyl-[4H]-1,3-benzodioxin-2-carboxylate and methyl 6-chloro-4-phenyl-4-benzyl-[4H]-1,3-benzodioxin-2-carboxylate and especially the isomer A of methyl 6-chloro-4-methyl-4-(3-trifluoromethylphenyl)-[4H]-1,3-benzodioxin-2-carboxylate.

The novel process of the invention for the preparation of a compound of formula I comprises reacting a compound of the formula

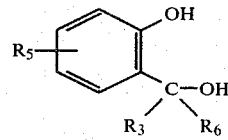

II wherein $R_3$, $R_5$ and $R_6$ have the above definitions with an alkali metal salt of a compound of the formula

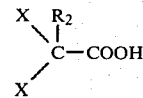

III wherein $R_2$ has the above definition and the Xs are selected from the group consisting of chlorine, bromine and iodine in the presence of a basic condensation agent to obtain the alkali metal salt of formula I which, if desired, may be treated with an acid to form the corresponding acid of formula I and, if desired, the acid or a functional derivative thereof may be reacted with an alcohol of the formula $R_1'OH$ wherein $R_1'$ is alkyl of 1 to 5 carbon atoms, dialkylaminoalkyl with alkyls of 1 to 5 carbon atoms or (2,2-dimethyl-1,3-dioxolan-4-yl)-methyl to obtain the corresponding esters of formula I and when $R_1'$ is (2,2-dimethyl-1,3-dioxolan-4-yl) methyl, the compound may be hydrolyzed to obtain the compound of formula I wherein $R_1$ is 2,3-dihydroxypropanol and the free acid of formula I may also be reacted with a base to obtain the corresponding salt and when $R_1$ is dialkylaminoalkyl, the compound of formula I may be reacted with an acid to form the acid addition salt thereof. The compounds of formula I may be recovered in the form of racemates, optically active isomers or mixtures of isomers.

In a preferred mode of the process, the alkali metal salt of the compound of formula III is sodium, potassium or lithium and the basic condensation agent is an alkali metal alcoholate such as sodium methylate, sodium ethylate or sodium tert.-butylate, or alkali metal hydride such as sodium hydride or potassium hydride or an alkali metal amide such as sodium amide, potassium amide or lithium amide or an alkali metal such as sodium. The condensation is preferably effected in an organic solvent such as benzene, toluene, xylene, ether, dioxane, dimethylformamide, tetrahydrofuran, hexamethylphosphortriamide and mixtures thereof.

The condensation of compounds of formulae II and III is preferably effected in the presence of a compound acting as a catalyst of the ether-courone type such as dibenzo-18-courone-6, dicyclohexyl-18-courone-6 or 18-courone-6 optionally in a mixture with an organic solvent such as dioxane and the reaction is effected at temperatures from −10° C. to reflux of the reaction mixture. Preferably, the compound of formula II is reacted with the basic condensation agent and then with the compound of formula III.

The functional derivatives of the acid of formula I may be the acid halide or ester prepared in a known manner. The esterification is preferably effected in an organic solvent such as benzene, xylene, toluene or ether. When the alkyl esters of formula I are prepared, the reaction is effected in the presence of an acid agent such as hydrochloric acid, p-toluene sulfonic acid or an acid resin. The esters of formula I when $R_1$ is methyl may be obtained by reacting the acid with diazomethane in an organic solvent. The hydrolysis may be effected with an acid such as hydrochloric acid.

The base used to form the salt of a compound of formula I may be a mineral or organic base such as sodium hydroxide, potassium hydroxide, lithium hydroxide, calcium hydroxide, aluminum hydroxide, sodium ethylate, potassium ethylate, ammonium hydroxide or an amine such as methylamine, ethylamine, propylamine, dimethylamine, diethylamine, dipropylamine, triethylamine, piperidine, morpholine, piperazine or pyrrolidine and the reaction is effected in at least one solvent such as water, ether, ethanol, acetone or ethyl acetate. The acid addition salts may be formed by known salification methods.

The compounds of formula II contain an asymmetric carbon atom and may be used in the form of racemates or an optically active isomer.

The different isomeric forms of the compounds of formula I may be separated by known methods. The racemates may be resolved into their optical enantiomers by known methods such as formation of salts with optically active bases. If the compounds of formula I exist in diastereoisomeric forms, racemate or optically active diastereoisomers named cis and trans, they may be separated, for example, by selective crystallization, counter-current extraction, chromatography or isomerization (with BF₃ in an appropriate solvent) or a combination of the said methods.

The novel hypolipemiant compositions of the invention are comprised of a hypolipemiantly effective amount of at least one compound of formula I and an inert pharmaceutical carrier or excipient. The compositions may be in the form of tablets, dragees, gelules, granules, suppositories and injectable solutions or suspensions.

Examples of suitable excipients are talc, arabic gum, lactose, starch, magnesium stearate, cacao butter, aqueous and non-aqueous vehicles, fatty bodies of animal or vegetable origin, paraffinic derivatives, glycols, preservatives and diverse wetting agents, dispersants or emulsifiers.

The compositions have a marked hypolipemiant activity and lower the plasmatic levels of lipids, triglycerides and cholesterol. They are useful for the treatment of acute or chronic hyperlipemia, cardiac insufficiencies of atheromatous origin or chronic angina states.

Among the preferred compositions of the invention are those where the active compounds are the compounds of formula $I_A$ wherein $R_3$ and $R_7$ are identical, those wherein $R_3$ and $R_7$ are identical and are either hydrogen or alkyl of 1 to 5 carbon atoms, the compounds of formula $I_B$ wherein $R_1$ and $R_2$ are individually hydrogen or methyl, $R_4$ and $R_5$ are individually hydrogen, chlorine, —CF₃, cyclohexyl, methoxy, or p-chlorophenoxy and $R_3$ is 2-propenyl, ethenyl, cyclohexyl, methyl or benzyl with the proviso that when $R_3$ is methyl, at least one of $R_4$ and $R_5$ is not hydrogen or chlorine and the compounds of formula $I_B$ wherein $R_1$ and $R_2$ are individually hydrogen or methyl, $R_4$ is hydrogen or —CF₃, $R_5$ is hydrogen, chlorine, —CF₃, cyclohexyl, methoxy or p-chlorophenoxy and $R_3$ is 2-propenyl, ethenyl, cyclohexyl, benzyl and methyl with the proviso that when $R_3$ is methyl, at least one of $R_4$ and $R_5$ is not hydrogen or chlorine and their salts.

Especially preferred compositions of the invention are those wherein the active compounds are racemates and optically active isomers of methyl 6-chloro-4-methyl-4-(3-trifluoromethylphenyl)-[4H]-1,3-benzodioxin-2-carboxylate and methyl 6-methoxy-4-methyl-4-phenyl-[4H]-1,3-benzodioxin-2-carboxylate and methyl 6-chloro-4-phenyl-4-benzyl-[4H]-1,3-benzodioxin-2-carboxylate and especially the isomer A of methyl 6-chloro-4-methyl-4-(3-trifluoromethylphenyl)-[4H]-1,3-benzodioxin-2-carboxylate.

The novel method of the invention for inducing hypolipemiant activity in warm-blooded animals, including humans, comprises administering to warm-blooded animals an hypolipemiantly effective amount of at least one compound of formula I. The compounds may be administered orally rectally or parenterally. The usual daily dose is 1 to 20 mg/kg depending on the method of administration and the specific compound.

The novel intermediate products of the invention are 5-chloro-α,α-diethyl-2-hydroxy-benzene-methanol, 5-chloro-2-hydroxy-α,α-dicyclohexyl-benzene-methanol, 4-chloro-2-(1-hydroxycyclohexyl)-phenol, 5-chloro-2-hydroxy-α,α-bis-(ethenyl)-benzene-methanol, 5-chloro-2-hydroxy-α-methyl-α-(3-trifluoromethylphenyl)-benzene-methanol, 5-chloro-2-hydroxy-α-(2-propenyl)-α-phenyl-benzene-methanol, 5-chloro-2-hydroxy-α-phenyl-α-ethenyl-benzene-methanol, 5-methyl-2-hydroxy-α-methyl-α-phenyl-benzene-methanol, 5-cyclohexyl-2-hydroxy-α-methyl-α-phenyl-benzene-methanol, 5-methoxy-2-hydroxy-α-methyl-α-phenyl-benzene-methanol, 5-chloro-2-hydroxy-α-phenyl-α-benzyl-benzene-methanol, 5-p-chlorophenoxy-2-hydroxy-α-methyl-α-phenyl-benzene-methanol and 5-chloro-2-hydroxy-α-cyclohexyl-α-phenyl-benzene-methanol.

The compounds of formula II are known or may be made by known methods. The compounds of formula II wherein $R_3$ and $R_6$ are hydrogen may be prepared by reduction of an ester of the formula

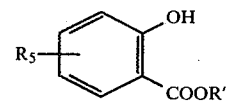   A wherein $R_5$ has the above definition and R' is alkyl of 1 to 5 carbon atoms with a mixed hydride in an organic solvent.

The compounds of formula II wherein $R_3$ and $R_6$ are identical and are alkyl of 1 to 6 carbon atoms, cyclohexyl or ethenyl may be prepared by reacting a mole of a compound of the formula

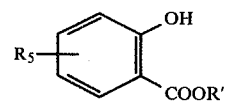   A with an excess (3 moles) of a compound of the formula $R_3MgX$ wherein X is a halogen and $R_3$ is alkyl, cyclohexyl or ethenyl.

The compounds of formula II wherein $R_3$ and $R_6$ together with the carbon atom they are attached form cyclohexyl may be prepared by the process of J. Org. Chem., Vol. 41 (1976), No. 15, p. 2628. The compounds of formula II wherein $R_3$ is hydrogen and $R_6$ is alkyl, of 1 to 6 carbon atoms, cyclohexyl or ethenyl may be prepared by reducing a compound of the formula

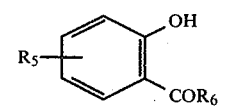   B wherein $R_5$ has the above definition with a mixed hydride in an organic solvent.

The compounds of formula II wherein $R_3$ and $R_6$ are different and are alkyl of 1 to 6 carbon atoms or cyclohexyl may be prepared by reacting a compound of formula B with a compound of the formula $R_3Mg$—Hal wherein Hal is chlorine or bromine and $R_3$ is alkyl of 1 to 6 carbon atoms or cyclohexyl. The compounds of formula II wherein $R_3$ is ethenyl and $R_6$ is alkyl or cyclohexyl may be prepared by reacting a compound of formula B with a compound of the formula $R_3$—Mg—Hal wherein $R_3$ is ethenyl.

The compounds of formula II wherein $R_3$ is hydrogen and $R_6$ is

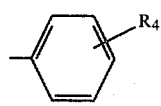

may be prepared by reducing a compound of the formula

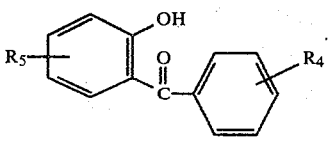

with a mixed hydride in an organic solvent.

The compounds of formula II wherein $R_3$ is 2-propenyl, ethenyl, cyclohexyl, benzyl or alkyl of 1 to 5 carbon atoms and $R_6$ is

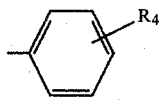

are not known and may be prepared by reacting a compound of formula A' in an organic solvent with a compound of the formula $R_3$—Mg—Hal or by reacting a compound of the formula

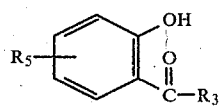

with a compound of the formula

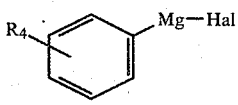

wherein $R_4$ and Hal have the above definitions.

The compounds of formulae A, A', B and B' which are not known may be prepared by the process of Fries, Organic Reactions, Vol. I, p. 342.

In the following examples there are described several preferred embodiments to illustrate the invention. However, it should be understood that the invention is not intended to be limited to the specific embodiments.

EXAMPLE 1

6-chloro-4,4-diethyl-[4H]-1,3-benzodioxin-2-carboxylic acid

STEP A: 5-chloro-α,α-diethyl-2-hydroxy-benzenemethanol

A solution of 124.8 g of ethyl iodide in 200 ml of anhydrous ether was added dropwise to a stirred dispersion of 19.5 g of magnesium turnings in 100 ml of anhydrous ether and the mixture was refluxed for 45 minutes and cooled in a ice water bath. A solution of 37.2 g of ethyl 5-chloro-salicylate in 120 ml of anhydrous ether was added thereto dropwise and the ether was distilled off while being replaced with 350 ml of anhydrous benzene. The solution was refluxed for 6 hours and was then cooled to room temperature and poured into an ice solution of 2 N hydrochloric acid. The decanted aqueous phase was washed 3 times with 75 ml of ether and the ether phase was washed twice with 100 ml of water until the wash water was neutral. The organic phase was dried over magnesium sulfate, was treated with activated carbon and was filtered. The filtrate was evaporated to dryness to obtain 38.3 g of raw product which was crystallized from 100 ml of cyclohexane and dried to obtain 27.5 g of 5-chloro-α,α-diethyl-2-hydroxy-benzene-methanol melting at 76° C.

Analysis: $C_{11}H_{15}O_2Cl$ Calculated: %C 61.54; %H 7.04; %Cl 16.51. Found: %C 61.4; %H 6.9; %Cl 16.6.

STEP B: 6-chloro-4,4-diethyl-[4H]-1,3-benzodioxin-2-carboxylic acid

A solution of 25.8 g of the product of Step A in 250 ml of anhydrous toluene was added dropwise with stirring to a mixture of 11.7 g of sodium amide in 100 ml of anhydrous toluene and the mixture was refluxed for 1 hour and was cooled to room temperature. 25 g of potassium dichloroacetate were added thereto and the suspension was refluxed for 6 hours. After cooling the mixture to room temperature, 200 ml of water were added thereto and the decanted phase was extracted twice with 80 ml of water. The aqueous extracts were extracted 3 times with 80 ml of ether and the combined aqueous phases were acidified with 100 ml of 2 N hydrochloric acid to obtain a sodium salt. The mixture was extracted 3 times with 100 ml of ether and the ether phases were washed 3 times with 80 ml of water. The sodium salt was extracted with aqueous saturated sodium bicarbonate solution and the organic phase was washed twice with 80 ml of water. The aqueous extraction phase was washed 3 times with 80 ml of ether and was acidified with 2 N hydrochloric acid. The liberated acid was extracted 3 times with 100 ml of ether and the organic phase was washed 3 times with 80 ml of water, was dried over magnesium sulfate, treated with carbon black and was evaporated to dryness under reduced pressure to obtain 28.3 g of raw product. The latter effloresced and was crystallized from hexane and was vacuum filtered to obtain 23.8 g of product. 13 g of the said product were crystallized from 250 ml of cyclohexane to obtain 8.2 g of 6-chloro-4,4-diethyl[4H]-1,3-benzodioxin-2-carboxylic acid melting at 108° C.

Analysis: $C_{13}H_{15}O_4Cl$. Calculated: %C 57.67; %H 5.58; %Cl 13.10. Found: %C 57.5; %H 5.7; %Cl 13.1.

RMN Spectrum (deuterochloroform-60 MHz):

hydrogen of —COOH at 588 Hz; 2-hydrogen at 329 Hz; hydrogen of $CH_2$ of 4-ethyl at 100 to 143 Hz; hydrogen of $CH_3$ of 4-ethyl at 34 to 62 Hz; aromatic hydrogens at 413 to 439 Hz.

EXAMPLE 2

6-chloro-4,4-dimethyl-[4H]-1,3-benzodioxin-2-carboxylic acid

A solution of 1.9 g of 5-chloro-α,α-dimethyl-2-hydroxybenzene-methanol in 15 ml of toluene was added dropwise to a stirred mixture of 0.8 g of sodium amide and 100 ml of toluene and the mixture was refluxed for 5 hours and was cooled to 50° C. 2 g of potassium dichloroacetate were added thereto and the mixture was refluxed for 6 hours and was cooled to 20° C. The mixture was poured into 200 ml of ice and 100 ml of N hydrochloric acid. The decanted aqueous phase was extracted 3 times with 50 ml of ether and the combined organic phases were made alkaline by stirring with 100 ml of 2 N sodium hydroxide solution. The organic phase was washed 3 times with 50 ml of N sodium hydroxide solution and the aqueous phase was acidified with concentrated hydrochloric acid and was extracted 3 times with 100 ml of ether. The ether phase was treated with 100 ml of 10% aqueous sodium bicarbonate solution and the aqueous phase was acidified with concentrated hydrochloric acid and was extracted 3 times with 50 ml of methylene chloride. The organic phase was washed with water until neutral, dried over magnesium sulfate and evaporated to dryness to obtain 2.1 g of 6-chloro-4,4-dimethyl-[4H]-1,3-benzodioxin-2-carboxylic acid which after crystallization from cyclohexane melted at 142° C.

Analysis: $C_{11}H_{11}ClO_4$. Calculated: %C 54.4; %H 4.6; %Cl 14.6. Found: %C 54.7; %H 4.7; %Cl 14.7.

RMN Spectrum (deuterochloroform-60 MHz):

2-hydrogen at 335 Hz; hydrogens of 4-methyl at 99–100 Hz; hydrogen of —COOH at ≃560 Hz; aromatic hydrogens at 415 to 441 Hz.

EXAMPLE 3

Methyl 6-chloro-4,4-dimethyl-[4H]-1,3-benzodioxin-2-carboxylate

STEP A: 6-chloro-4,4-dimethyl-[4H]-1,3-benzodioxin-2-carboxylic acid chloride

A solution of 4 g of thionyl chloride in 30 ml of anhydrous benzene was added dropwise at room temperature with stirring to a mixture of 7.5 g of the product of Example 2, 70 ml of anhydrous benzene and 4.2 ml of triethylamine and the mixture was refluxed for 4 hours and cooled to room temperature. The mixture was filtered and the recovered product was washed with benzene. The filtrate was evaporated to dryness under reduced pressure to obtain 7.9 g of raw product in the form of an oil which was distilled to obtain 6.05 g of 6-chloro-4,4-dimethyl-[4H]-1,3-benzodioxin-2-carboxylic acid chloride with a boiling point of 112° C. at 0.05 mm Hg.

Analysis: $C_{11}H_{10}O_3Cl_2$. Calculated: %C 50.60; %H 3.86; %Cl 27.16. Found: %C53.1; %H 4.2; %Cl 25.19.

STEP B: Methyl 6-chloro-4,4-dimethyl-[4H]-1,3-benzodioxin-2-carboxylate

A solution of 5.9 g of 6-chloro-4,4-dimethyl-[4H]-1,3-benzodioxin-2-carboxylic acid chloride in 30 ml of anhydrous benzene was added dropwise to a stirred mixture of 0.8 g of methanol, 30 ml of anhydrous benzene and triethylamine and the mixture was stirred for 2 hours at room temperature and was filtered. The filter was washed with benzene and the filtrate was washed with an aqueous saturated sodium bicarbonate solution and then with water until the wash water was neutral, dried over magnesium sulfate and evaporated to dryness under reduced pressure. The 5.1 g of residue was crystallized from cyclohexane to obtain, after drying, 2.6 g of methyl 6-chloro-4,4-dimethyl-[4H]-1,3-benzodioxin-2-carboxylate melting at 92° C.

Analysis: Calculated: %C 56.15; %H 5.10; %Cl 13.81. Found: %C56.0; %H 5.1; %Cl 13.7.

RMN Spectrum (deuterochloroform-90 MHz):

peaks at 492 Hz (2-hydrogen); at 351 Hz (hydrogens of COOCH$_3$); at 145 and 148 Hz (hydrogens of 4-CH$_3$); at 617 to 646 Hz (aromatic hydrogens).

EXAMPLE 4

6-chloro-4,4-dicyclohexyl-[4H]-1,3-benzodioxin-2-carboxylic acid

STEP A: 5-chloro-α,α-dicyclohexyl-2-hydroxybenzene-methanol 270 ml of a solution of cyclohexyl magnesium bromide titrating 1.3 M/liter in ether were added dropwise with stirring at room temperature to a mixture of 18.7 g of methyl 5-chloro-2-hydroxy-benzoate in 150 ml of ether and the ether was distilled while replacing it with 270 ml of benzene. The mixture was then refluxed for 20 hours and was cooled and poured into a mixture of 500 g of ice and 300 ml of an aqueous solution containing 105 g of ammonium chloride. The mixture was extracted once with 250 ml of ether, twice with 150 ml of ether and 3 times with 100 ml of methylene chloride. The organic phases were washed 3 times with 100 ml of water, were dried over magnesium sulfate in the presence of activated carbon and was evaporated to dryness. The residue was taken up in 50 ml of cyclohexane and the mixture was vacuum filtered. The product was dried to obtain 20,200 g of 5-chloro-α,α-dicyclohexyl-2-hydroxybenzene-methanol melting at 230° C.

Analysis: Calculated: %C 70.68; %H 8.43; %Cl 10.98. Found: %C 70.5; %H 8.6; %Cl 11.0.

STEP B: 6-chloro-4,4-dicyclohexyl-[4H]-1,3-benzodioxincarboxylic acid

A mixture of 5.8 g of dichloroacetic acid in 60 ml of anhydrous dioxane was added with stirring at room temperature to a mixture of 40 ml of dioxane, 5.1 g of sodium hydride in a 50% oil emulsion and 0.720 g of dibenzo-18-courone-6 and then a solution of 9.7 g of the product of Step A in 60 ml of anhydrous dioxane was added dropwise thereto with stirring. The mixture was heated to 80° C. until hydrogen evolution ceased and was then heated at 90° C. for 6 hours and was cooled. The mixture was poured into ice and the aqueous phase was washed 3 times with 100 ml of ether and was acidified with 15 ml of concentrated hydrochloric acid. The aqueous phase was extracted 4 times with 100 ml of methylene chloride and the combined organic extracts were extracted 4 times with 100 ml of a 5% sodium bicarbonate aqueous solution. The mixture was filtered and the sodium salt was taken up in 150 ml of water and 100 ml of concentrated hydrochloric acid. The mixture was stirred overnight at room temperature and was extracted 4 times with 100 ml of methylene chloride. The decanted organic phase was washed with water until the wash water was neutral, dried over magnesium sulfate and evaporated to dryness under reduced pressure. The residue was taken up in 50 ml of methylene chloride and was vacuum filtered. The crystalline product was dried to obtain 4.55 g of 6-chloro-4,4-dicyclohexyl-[4H]-1,3-benzodioxin-2-carboxylic acid melting at 208° C.

Analysis: Calculated: %C 66.57; %H 7.18; %Cl 9.35. Found: %C 66.7; %H 7.3; %Cl 9.4.

RMN Spectrum (deuterochloroform-60 MHz):

peaks at 320 Hz (2-hydrogen); at 40 to 160 Hz (hydrogens of CH$_2$); at 413 to 438 Hz (aromatic hydrogens).

EXAMPLE 5

6-chloro-spiro-[cyclohexane-1-4'-(4H)-1,3-benzodioxin]-2'-carboxylic acid

STEP A: 4-chloro-2(1-hydroxycyclohexyl)-phenol

A mixture of 20.75 g of 2-bromo-4-chloro-phenol, 200 ml of anhydrous tetrahydrofuran cooled to −30° C. was stirred and then 172 ml of a solution of butyllithium in hexane titrating 1.16 M/l were added thereto with stirring over 45 minutes at −30° C. The mixture was stirred for 4½ hours at −30° C. and was then cooled to −78° C. at which 10.35 ml of cyclohexanone were added over one hour. The mixture was stirred at −75° to −78° C. for 17 hours and the temperature was then allowed to return to room temperature. The mixture was poured into a water-concentrated hydrochloric acid mixture and was then extracted with ether. The ether extracts were washed with water, dried over magnesium sulfate and evaporated to dryness under reduced pressure to obtain 25 g of raw residue. The latter was chromatographed over silica gel H under pressure and elution with methylene chloride yielded 7 g of 4-chloro-2-(1-hydroxycyclohexyl)-phenol melting at 110° C.

Analysis: Calculated: %C 63.57; %H 6.67; %Cl 15.63. Found: %C 63.6; %H 6.9; %Cl 15.4.

STEP B: 6-chloro-spiro-(cyclohexane-1-4'-(4H)-1,3-benzodioxin)-2'-carboxylic acid 10 g of the product of Step A were added over 45 minutes at 22° C. to a mixture of 150 ml of anhydrous toluene and 4.2 g of sodium hydride as a 50% oil suspension with the final temperature being 35° C. and the mixture was refluxed for 6½ hours and was cooled to 50° C. 8.4 g of potassium dichloroacetate were added all at once to the mixture and the mixture was refluxed under argon with stirring overnight. The mixture was cooled and hydrolyzed with water. The decanted aqueous phase was washed twice with 200 ml of ether and was acidified with hydrochloric acid and was extracted 3 times with 300 ml of ether. The ether phase was extracted 3 times with 300 ml of an aqueous sodium bicarbonate solution and the aqueous phase was washed 3 times with 300 ml of ether and was acidified with hydrochloric acid. The mixture was extracted with ether and the ether phase was washed with water, dried over magnesium sulfate, treated with activated carbon and was filtered. The filtrate was evaporated to dryness and the 10 g of residue was crystallized from a 10-2 cyclohexane-ethyl acetate mixture to obtain 7.5 g of 6-chloro-spiro-(cyclohexane-1-4'-(4H)-1,3-benzodioxin)-2'-carboxylic acid melting at 180° C.

Analysis: $C_{14}H_{15}ClO_4$. Calculated: %C 59.47; %H 5.34; %Cl 12.54. Found: %C 59.5; %H 5.4; %Cl 12.8.

RMN Spectrum (deuterochloroform-90 MHz):

peaks at 490 Hz (2-hydrogen); at 617 to 648 Hz (aromatic hydrogens); at ≃900 Hz (hydrogen of OH); at ≃90 to 200 Hz (hydrogen (CH$_2$)).

EXAMPLE 6

4,4-bis-ethenyl-6-chloro-[4H]-1,3-benzodioxin-2-carboxylic acid

STEP A: 5-chloro-α,α-bis-ethenyl-2-hydroxybenzene-methanol

A solution of methyl 5-chlorosalicylate in 200 ml of anhydrous ether was added dropwise with stirring at 10° C. to a mixture of 250 ml of a tetrahydrofuran solution titrating 2.6 M/liter of ethenyl magnesium chloride and 300 ml of anhydrous ether and the mixture was allowed to return to room temperature and was then stirred overnight at room temperature. The mixture was poured into a liter of iced water containing 10% of ammonium chloride and the decanted aqueous phase was extracted twice with 150 ml of ether. The organic extracts were washed 3 times with 100 ml of water, dried over magnesium sulfate, treated with activated carbon and was filtered. The filtrate was evaporated to dryness under reduced pressure and the 39 g of oil residue was chromatographed under pressure over silica gel H. Fractional elution with methylene chloride and evaporation of the solvent yielded 13.9 g of 5-chloro-α,α-bis-ethenyl-2-hydroxybenzene-methanol.

Analysis: $C_{11}H_{11}O_2Cl$. Calculated: %C 62.72; %H 5.26; %Cl 16.83. Found: %C 62.9; %H 5.4; %Cl 16.8.

STEP B: 4,4-bis-ethenyl-6-chloro-(4H)-1,3-benzodioxin-2-carboxylic acid

A solution of the product of Step A in 100 ml of anhydrous toluene was added dropwise at room temperature with stirring to a mixture of 4 g of sodium amide and 50 ml of anhydrous toluene and the mixture was refluxed for 90 minutes and was then cooled to room temperature. 6.7 g of potassium dichloroacetate were added thereto and the mixture was refluxed with stirring for 5 hours and was then cooled to room temperature. 200 ml of water were added thereto and the decanted organic phase was extracted twice with 80 ml of water. The aqueous extracts were washed 3 times with 50 ml of ether, was acidified with hydrochloric acid and was extracted 3 times with 80 ml of ether. The ether extract was washed twice with 50 ml of water and was extracted with an aqueous 5% sodium bicarbonate solution and 3 times with 80 ml of water. The combined aqueous extracts were washed twice with 80 ml of ether and were acidified with 2 N hydrochloric acid. The aqueous phase was extracted 3 times with 100 ml of ether and ether extracts were washed twice with 50 ml of water, dried over magnesium sulfate, treated with activated carbon and filtered. The filtrate was evaporated to dryness under reduced pressure and the 6 g of residue was crystallized from 150 ml of a 4-1 cyclohexane-ethylacetate mixture to obtain 2.9 g of 4,4-bis-ethenyl-6-chloro-(4H)-1,3-benzodioxin-2-carboxylic acid melting at 144° C.

Analysis: Calculated: %C 58.55; %H 4.16; %Cl 13.29. Found: %C 58.3; %H 4.3; %Cl 13.1.

RMN Spectrum (deuterochloroform-60 MHz):

peaks at ≃360 Hz (hydrogen of COOH); at 335 Hz (2-hydrogen); at 300 to 381 Hz (hydrogens of —CH=CH$_2$); at 414 to 441 Hz (aromatic hydrogens).

EXAMPLE 7

Potassium[4H]-1,3-benzodioxin-2-carboxylate

A solution of 24.6 ml of dichloroacetic acid in 150 ml of anhydrous dioxane was added dropwise at room temperature with vigorous stirring to a mixture of 38.4 g of sodium hydride as a 50% oil suspension, 10 g of dibenzo-18-courone-6 and 385 ml of anhydrous dioxane and the mixture was heated at 90° C. for 10 hours and was then cooled to room temperature. The mixture was poured into ice and the aqueous phase was acidified with 2 N hydrochloric acid and was extracted 3 times with 200 ml of ether. The ether extracts were washed with 80 ml of water and were extracted with an aqueous saturated sodium bicarbonate solution and then 3 times with 150 ml of water. The combined aqueous extracts were washed 3 times with 100 ml of ether and was acidified with 2 N hydrochloric acid and extracted 3 times with 150 ml of ether. The combined ether extracts were washed 3 times with 80 ml of water, were dried over magnesium sulfate, treated with activated carbon and filtered. The filtrate was evaporated to dryness under reduced pressure and the 53 g of oil residue were dissolved in 50 ml of methanol. A solution obtained by dissolving 11.2 g of potassium hydroxide pastilles in 200 ml of methanol by stirring at room temperature for 15 minutes was added thereto dropwise at less than 10° C. and the mixture was filtered. The recovered product was washed with ether to obtain 19.4 g of potassium[4H]-1,3-benzodioxin-2-carboxylate.

Analysis: $C_9H_7O_4$. Calculated: %C 49.53; %H 3.23. Found: %C 49.9; %H 3.3.

RMN Spectrum (deuterochloroform-60 MHz):

peaks at 322 Hz (2-hydrogen); at 304 Hz (4-hydrogens); at 430 Hz (aromatic hydrogens).

EXAMPLE 8

[4H]-1,3-benzodioxin-2-carboxylic acid 11.2 ml of 2 N hydrochloric acid were added dropwise at 10° C. to a solution of 4.65 g of the product of Example 7 in 93 ml of an aqueous saturated sodium chloride solution and the mixture was stirred at room temperature for 2 hours and was extracted 3 times with 100 ml of ether. The ether extracts were washed twice with 50 ml of an aqueous saturated sodium chloride solution, dried over sodium sulfate and was evaporated to dryness to obtain 3.8 g of residue which were crystallized from 220 ml of cyclohexane to obtain 3.4 g of [4H]-1,3-benzodioxin-2-carboxylic acid melting at 88° C.

Analysis: $C_9H_8O_4$. Calculated: %C 60.00; %H 4.48. Found: %C 60.0; %H 4.5.

RMN Spectrum (deuterochloroform-90 MHz):

peaks at 455 Hz (4-hydrogens); at 498 Hz (2-hydrogen); at 560 Hz (hydrogen of COOH); at 620 to 660 Hz (aromatic hydrogens).

EXAMPLE 9

Ethyl 6-chloro-4,4-dimethyl-[4H]-1,3-benzodioxin-2-carboxylate

A solution of 9.4 g of 6-chloro-4,4-dimethyl-[4H]-1,3-benzodioxin-2-carboxylic acid chloride in 50 ml of anhydrous benzene was added dropwise at room temperature with stirring to a mixture of 2.3 g of ethanol, 30 ml of anhydrous benzene and 3.03 g of triethylamine and the solution was stirred for 6 hours at room temperature and was vacuum filtered. The filtrate was washed with 70 ml of an aqueous saturated sodium bicarbonate solution and twice with 70 ml of water, was dried over magnesium sulfate, treated with activated carbon and filtered. The filtrate was evaporated to dryness under reduced pressure and the 8.4 g of residue were chromatographed over silica gel H. Fractional elution with methylene chloride and evaporation of the solvent yielded 5.3 g of ethyl 6-chloro-4,4-dimethyl-[4H]-1,3-benzodioxin-2-carboxylate in the form of an oil which crystallized at less than 50° C.

Analysis: $C_{13}H_{15}ClO_4$. Calculated: %C 57.68; %H 5.58; %Cl 13.10. Found: %C 57.5; %H 5.6; %Cl 12.9.

RMN Spectrum (deuterochloroform-60 MHz):

peaks at 76-83-90 and 253-260-274 Hz (hydrogens of $COOC_2H_5$); at 97.5 and 99 Hz (hydrogens of 4-$CH_3$); at 330 Hz (2-hydrogen); at 413 to 441 Hz (aromatic hydrogens).

EXAMPLE 10

2-(diethylamino)-ethyl 6-chloro-4,4-dimethyl-[4H]-1,3-benzodioxin-2-carboxylate hydrochloride A solution of 3.4 g of 6-chloro-4,4-dimethyl-[4H]-1,3-benzodioxin-2-carboxylic acid chloride in 50 ml of anhydrous benzene was added dropwise with stirring at room temperature to a mixture of 250 ml of 2-diethylamino-ethanol and 50 ml of anhydrous benzene and the mixture was stirred for 5 hours at room temperature and was then filtered. The recovered product was washed with ether and dried to obtain 7.2 g of product which was crystallized from 70 ml of isopropanol and was dried to obtain 3.3 g of 2-(diethylamino)-ethyl 6-chloro-4,4-dimethyl-[4H]-1,3-benzodioxin-2-carboxylate hydrochloride melting at 159° C.

Analysis: $C_{17}H_{25}NO_4Cl_2$. Calculated: %C 53.97; %H 6.66; %Cl 18.74; %N 3.70. Found: %C 54.0; %H 6.7; %Cl 18.7; %N 3.7.

RMN Spectrum (deuterochloroform-60 MHz):

peaks at ≃407 to 435 Hz (aromatic hydrogens); at 95 and 98.5 Hz (hydrogens of 4-$CH_3$); at ≃80-87-94 Hz (hydrogens of $CH_3$ of ethyl); at 184-220 Hz (hydrogens of $CH_2$-N); at 286-291-296 Hz (hydrogens of $COOCH_2$); at 333 Hz (2-hydrogen); at 590 Hz (mobile hydrogen).

EXAMPLE 11

(2,2-dimethyl-1,3-dioxolan-4-yl)-methyl 6-chloro-4,4-dimethyl-[4H]-1,3-benzodioxin-2-carboxylate A solution of 33.5 g of 6-chloro-4,4-dimethyl-[4H]-1,3-benzodioxin-2-carboxylic acid chloride in 250 ml of anhydrous benzene was added dropwise with stirring at room temperature to a mixture of 17 g of 2,2-dimethyl-4-hydroxymethyl-1,3-dioxolane, 150 ml of anhydrous benzene and 13 g of triethylamine and the mixture was stirred for 5 hours and was filtered. The filtrate was washed twice with 80 ml of water, was dried over magnesium sulfate and evaporated to dryness under reduced pressure to obtain 41.8 g of a brown oil which was pressure chromatographed over silica gel. Elution with methylene chloride yielded 17.3 g of (2,2-dimethyl-1,3-dioxolan-4-yl)-methyl 6-chloro-4,4-dimethyl-[4H]-1,3-benzodioxin-2-carboxylate which after crystallization from hexane melted at 45° C.

Analysis: $C_{17}H_{21}ClO_6$. Calculated: %C 57.22; %H 5.93; %Cl 9.94. Found: %C 56.9; %H 6.1; %Cl 10.0.

RMN Spectrum (deuterochloroform-60 MHz):

peaks at 323 Hz (2-hydrogen); at 215-265 Hz (hydrogens of $COOCH_2$—CH); at 215-245 Hz (hydrogens of —$CH_2O$—); at 80-84 Hz (hydrogens of methyl, of (2,2-dimethyl-1,3-dioxolan-4-yl)); at 93-95 Hz (hydrogens of 4-$CH_3$); at 401 to 430 Hz (aromatic hydrogens).

EXAMPLE 12

2,3-dihydroxypyranyl 6-chloro-4,4-dimethyl-[4H]-1,3-benzodioxin-2-carboxylate 0.5 ml of water and 0.2 ml of 2 N hydrochloric acid were added to a solution of 0.55 g of the product of Example 11 in 20 ml of dioxane and the mixture was heated at 75° C. for 2 hours and was then evaporated to dryness under reduced pressure. The residue was taken up in ether and the organic phase was washed with water until the wash water was neutral, dried and evaporated to dryness under reduced pressure to obtain 0.3 g of 2,3-dihydroxypyranyl 6-chloro-4,4-dimethyl-[4H]-1,3-benzodioxin-2-carboxylate in the form of an oil.

RMN Spectrum (deuterochloroform-60 MHz):

peaks at 330 Hz (2-hydrogen); at 260-265 Hz (hydrogens of —COO—$CH_2$—CH′—); at 225-250 Hz and 220-225 Hz (hydrogens of —CH—$CH_2$); at 195 Hz (hydrogens of OH); at 96-98 Hz (hydrogens of 4-$CH_3$); at 424 to 434 Hz (aromatic hydrogens).

EXAMPLE 13

6-chloro-2,4,4-trimethyl-[4H]-1,3-benzodioxin-2-carboxylic acid

A mixture of 5.91 g of sodium hydride in a 50% oil suspension, 60 ml of anhydrous dioxane, 0.550 g of courone ether and 15.55 g of sodium 2,2-dichloropropionate was stirred at room temperature for 20 minutes and then a solution of 11 g of 5-chloro-2-hydroxy-α,α-dimethyl-phenylcarbinol in 110 ml of dioxane was added thereto dropwise. The mixture was slowly heated to 95° C. and was held at 95° C. for 8 hours. The mixture was cooled and was poured into ice and the mixture was washed with ether and acidified with 30 ml of concentrated hydrochloric acid. The mixture was extracted with methylene chloride and the organic phase was washed with water and was extracted with an aqueous saturated sodium bicarbonate solution. The aqueous extract was acidified with 70 ml of concentrated hydrochloric acid and was extracted with methylene chloride. The organic phase was washed with water, dried and evaporated to dryness under reduced pressure to obtain 14.2 g of 6-chloro-2,4,4-trimethyl-[4H]-1,3-benzodioxin-2-carboxylic acid in the form of a brown oil.

RMN Spectrum (dueterochloroform-60 MHz):

peaks at 408–417 Hz (8-hydrogen); at 417–435 Hz (other aromatic hydrogens); at 92–93–104 Hz (hydrogens of methyls); at ≃490 Hz (hydrogen of hydroxy).

EXAMPLE 14

Methyl 6-chloro-2,4,4-trimethyl-[4H]-1,3-benzodioxin-2-carboxylate 7.84 g of the etherate of boron trifluoride were added dropwise at 15° C. to a mixture of 14.2 g of the product of Example 13 in 145 ml of methanol and the mixture was stirred overnight at room temperature. 500 ml of an aqueous saturated sodium chloride solution were added to the mixture which was then extracted with methylene chloride. The organic phase was washed with aqueous saturated sodium bicarbonate solution, then with water until the wash water was neutral, dried and evaporated to dryness under reduced pressure to obtain 12.2 g of residue which was crystallized from petroleum ether to obtain 6.9 g of methyl 6-chloro-2,4,4-trimethyl-[4H]-1,3-benzodioxin-2-carboxylate melting at 89° C.

Analysis: $C_{13}H_{15}ClO_4$; molecular weight=270.713. Calculated: %C 57.66; %H 5.58; %Cl 13.10. Found: %C 57.8; %H 5.8; %Cl 13.1.

RMN Spectrum (deuterochloroform-60 MHz):

peaks at 409–418 Hz (8-hydrogen); at 425–427 Hz and 434–436 Hz (7-hydrogen); at 419–421 Hz (5-hydrogen); at 90–91–103.5 Hz (hydrogens of methyls); at 220 Hz (hydrogens of COOCH$_3$).

EXAMPLE 15

6-chloro-4-methyl-4-hexyl-[4H]-1,3-benzodioxin-2-carboxylic acid (2 diastereoisomeric racemates)

STEP A: 5-chloro-2-hydroxy-α-methyl-α-hexyl-phenyl carbinol 385 ml of an ether solution titrating 1.1 M/liter of hexyl magnesium bromide were added dropwise with stirring to a mixture of 32 g of 5-chloro-2-hydroxy-acetophenone in 400 ml of anhydrous ether and the mixture was refluxed with stirring for 6 hours and was cooled. The mixture was poured into 500 ml of an iced aqueous 10% ammonium chloride solution and the mixture was extracted with ether. The ether extracts were washed with water until the wash water was neutral and dried to obtain 46.2 g of an oily product. The latter was pressure chromatographed over silica gel and was eluted with methylene chloride to obtain 21.8 g of 5-chloro-2-hydroxy-α-methyl-α-hexyl-phenyl carbinol.

STEP B: 6-chloro-4-methyl-4-hexyl-[4H]-1,3-benzodioxin-2-carboxylic acid

A mixture of 16.25 g of dichloroacetic acid in 110 ml of anhydrous dioxane was added at room temperature with stirring to a mixture of 14.5 g of sodium hydride as a 50% oil suspension, 150 ml of anhydrous dioxane and 1.1 g of courone ether and the temperature was returned to room temperature. Then, a solution of 21.8 g of the product of Step A in 250 ml of anhydrous dioxane was added thereto dropwise and the mixture was slowly heated to 100° C. and held there overnight. The mixture was cooled and was poured into ice and the mixture was washed with ether and was acidified with 30 ml of concentrated hydrochloric acid. The mixture was extracted with ether and the ether extracts were washed with water, dried and evaporated to dryness under reduced pressure to obtain 41.9 g of raw 6-chloro-4-methyl-4-hexyl-[4H]-1,3-benzodioxin-2-carboxylic acid in the form of 2-diasteroisomeric racemates.

RMN Spectrum (deuterochloroform-90 MHz):

peaks at 619 to 669 Hz (aromatic hydrogens); at 140 and 147 Hz (hydrogens of 4-CH$_3$); at ∼76 Hz (6-hydrogens of hexyl); at 489 and 493.5 Hz (2-hydrogen); at ∼720 Hz (hydrogen of OH).

EXAMPLE 16

Methyl 6-chloro-4-methyl-4-hexyl-[4H]-1,3-benzodioxin-2-carboxylate 12.05 g of the etherate of boron trifluoride were added dropwise with stirring at 15° C. to a mixture of 26.5 g of the product of Example 15 in 270 ml of methanol and the mixture was held overnight at room temperature and was then poured into an aqueous saturated sodium chloride solution. The mixture was extracted with methylene chloride and the organic extracts were washed with an aqueous saturated sodium carbonate solution, then with water until the wash water was neutral, dried and evaporated to dryness under reduced pressure. The 27.1 g of yellow oil was pressure chromatographed over silica gel and was eluted with a 5-95 isopropyl etherpetroleum ether mixture to obtain 7.15 g of isomer A and 7.15 g of isomer B of methyl 6-chloro-4-methyl-4-hexyl-[4H]-1,3-benzodioxin-2-carboxylate.

Analysis: $C_{17}H_{23}ClO_4$; molecular weight=326.828. Calculated: %C 62.47; %H 7.1; %Cl 10.85. Found: %C 62.8; %H 7.2; %Cl 11.1.

Isomer A-RMN Spectrum (deuterochloroform-90 MHz):

peaks at 619–627 Hz (8-hydrogen); at 638–640 Hz and 647–649 Hz (7-hydrogen); at 631–633 Hz (5-hydrogen); at 139 Hz (hydrogens of 4-CH$_3$); at ∼80 Hz (6-hydrogens of hexyl); at 351 Hz (hydrogens of COOCH$_3$); at 493 Hz (2-hydrogen).

Isomer B-RMN Spectrum (deuterochloroform-90 MHz):

peaks at 620–628 Hz (8-hydrogen); at 639–641 Hz and 647–649 Hz (7-hydrogen); at 630–632 Hz (5-hydrogen); at 146 Hz (hydrogens of 4-CH$_3$); at ∼76 Hz (6-hydrogens of hexyl); at 352.5 Hz (hydrogens of COOCH$_3$); at 489 Hz (2-hydrogen).

EXAMPLE 17

6-chloro-4-methyl-4-(3-trifluoromethylphenyl)-[4H]-1,3-benzodioxin-2-carboxylic acid (mixture of 2 diastereoisomeric racemates)

STEP A: 5-chloro-2-hydroxy-α-methyl-α-(3-trifluoromethylphenyl)-benzene-methanol A stirred, cooled mixture of 23.1 g of 2-hydroxy-5-chloro-acetophenone and 200 ml of anhydrous ether was admixed dropwise with 760 ml of an ether solution titrating 0.42 M/liter of m-trifluoromethyl-phenyl magnesium bromide and 250 ml of 2 N hydrochloric acid were added to the mixture while cooling it in an ice bath. The decanted organic phase was washed with water, dried over magnesium sulfate and evaporated to dryness to obtain 47.4 g of raw product. The latter was empasted with cyclohexane and stirred for one hour at room temperature. The mixture was vacuum filtered and the product was washed with cyclohexane and was dried to obtain 35 g of 5-chloro-2-hydroxy-α-methyl-α-(3-trifluoromethylphenyl)-benzene-methanol melting at 115° C.

Analysis: $C_{15}H_{12}O_2F_3Cl$. Calculated: %C 56.88; %H 3.81; %F 17.99; %Cl 11.99. Found: %C 56.9; %H 3.8; %F 17.8; %Cl 11.0.

STEP B: 6-chloro-4-methyl-4-(3-trifluoromethylphenyl)-[4H]-1,3-benzodioxin-2-carboxylic acid (mixture of 2 diastereoisomeric racemates A solution of 19.33 g of dichloroacetic acid in 200 ml of anhydrous dioxane was added dropwise at room temperature with stirring to a mixture of 16.8 g of sodium hydride in a 50% oil suspension, 150 ml of anhydrous dioxane and 1.6 g of dibenzo-18-courone-6 and then a solution of 31.7 g of 5-chloro-2-hydroxy-α-methyl-α-(3-trifluoromethylphenyl)-benzene-methanol in 200 ml of dioxane was added thereto dropwise. The mixture was progressively heated to 80° C. and held there for 5 hours and then was cooled. The mixture was poured into ice and the aqueous phase was extracted with 400 ml of ether and was then acidified with 30 ml of concentrated hydrochloric acid. The aqueous phase was then extracted 3 times with 350 ml of methylene chloride and the organic extracts were washed twice with 200 ml of water and was extracted 4 times with 250 ml of an aqueous saturated sodium bicarbonate solution. The aqueous phase was washed with 200 ml of ether and was acidified with 80 ml of concentrated hydrochloric acid. The aqueous phase was then extracted 4 times with 200 ml of water and the ether extracts were washed 5 times with 100 ml of water, dried over magnesium sulfate, treated with activated carbon and filtered. The filtrate was evaporated to dryness under reduced pressure to obtain 28.4 g of raw 6-chloro-4-methyl-4-(3-trifluoromethylphenyl)-[4H]-1,3-benzodioxin-2-carboxylic acid (mixture of 2 diastereoisomeric racemates).

RMN Spectrum (deuterochloroform-60 MHz):

peaks at 117 Hz (hydrogens of 4-CH$_3$-isomer A); at 127 Hz (hydrogens of 4-CH$_3$-isomer B); at 307 Hz (2-hydrogen-isomer A); at 341 Hz (2-hydrogen-isomer B).

EXAMPLE 18

Isomer A of methyl 6-chloro-4-methyl-4-(3-trifluoromethylphenyl)-[4H]-1,3-benzodioxin-4-carboxylate A mixture of 28.4 g of the product of Example 17, 350 ml of methanol and 150 g of a strong acid resin was refluxed for 16 hours and the suspension was then cooled and filtered. The filtrate was washed with ether and was evaporated to dryness under reduced pressure. The residue was taken up in ether and the organic phase was washed with an aqueous 5% sodium bicarbonate solution and then with water until the wash water was neutral. The solution was dried over magnesium sulfate and was evaporated to dryness to obtain an oil which was dissolved in 250 ml of methylene chloride. 8 ml of the etherate of boron trifluoride were added to the solution and the mixture was stirred at room temperature for 4 days. The solution was poured into an ice-water mixture and the decanted organic phase was wahed with water, dried over magnesium sulfate, treated with activated carbon and evaporated to dryness to obtain 24.25 g of a mixture of A and B isomers of methyl 6-chloro-4-methyl-4-(3-trifluoromethylphenyl)-[4H]-1,3-benzodioxin-2-carboxylate. The mixture was treated with 30 ml of methanol and was vacuum filtered. The product was washed with methanol and was dried to obtain 8.9 g of isomer A of methyl 6-chloro-4-methyl-4-(3-trifluoromethylphenyl)-[4H]-1,3-benzodioxin-4-carboxylate melting at 98° C.

Analysis: $C_{18}H_{14}ClF_3O_4$. Calculated: %C 55.90; %H 3.64; %F 14.73; %Cl 9.16. Found: %C 56.0; %H 3.7; %F 14.7; %Cl 9.4.

RMN Spectrum (deuterochloroform-60 MHz):

peaks at 116 Hz (hydrogens of 4-CH$_3$); at 232 Hz (hydrogens of COOCH$_3$); at 306 Hz (2-hydrogen); at 414 to 460 Hz (aromatic hydrogens).

EXAMPLE 19

6-chloro-4-phenyl-4-(2-propenyl)-[4H]-1,3-benzodioxin-2-carboxylic acid (mixture of 2 diastereoisomeric racemates)

STEP A: 5-chloro-2-hydroxy-α-(2-propenyl)-α-phenyl-benzenemethanol 360 ml of an ether solution titrating 1 M/liter of allyl magnesium bromide were added dropwise with stirring to a mixture of 40 g of 2-hydroxy-5-chloro-benzophenone and 400 ml of anhydrous ether and the suspension was iced and stirred at room temperature for 16 hours. 180 ml of 2 N hydrochloric acid were added to the mixture and the decanted organic phase was washed with water, dried over mangesium sulfate and evaporated to dryness under reduced pressure. The oil residue was chromatographed over silica gel and was eluted with methylene chloride to obtain 18.9 g of 5-chloro-2-hydroxy-α-(2-propenyl)-α-phenyl-benzene-methanol.

Analysis: $C_{16}H_{15}O_2Cl$. Calculated: %C 69.95; %H 5.5; %Cl 12.9. Found: %C 69.9; %H 5.4; %Cl 12.9.

STEP B: 6-chloro-4-phenyl-4-(2-propenyl)-[4H]-1,3-benzodioxin-2-carboxilic acid (mixture of 2 diastereoisomeric racemates)

A mixture of 8 ml of dichloroacetic acid in 50 ml of dioxane was added over 20 minutes at 25°-35° C. to a mixture of 125 ml of dioxane, 0.8 g of dibenzo-18-courone-6 and 12 g of sodium hydride as a 50% oil suspension and then a solution of 18 g of the product of Step A in 75 ml of anhydrous dioxane was added thereto over 15 minutes. The mixture was heated at 90° C. for 4 hours and was then cooled and poured into ice. The aqueous phase was washed twice with 400 ml of ether and was acidified with hydrochloric acid. The aqueous phase was then extracted 3 times with 500 ml of ether and the combined ether phases were extracted 3 times with 400 ml of an aqueous sodium bicarbonate solution.

The aqueous phase was acidified with hydrochloric acid and was extracted 3 times with 500 ml of ether. The ether phase was washed with water until the wash water was neutral, dried over magnesium sulfate and evaporated to dryness under reduced pressure to obtain 20 g of raw 6-chloro-4-phenyl-4-(2-propenyl)-[4H]-1,3-benzodioxin-2-carboxylic acid (mixture of 2 diastereoisomeric racemates) in the form of a resin.

EXAMPLE 20

Isomer A of methyl 6-chloro-4-phenyl-4-(2-propenyl)-[4H]-1,3-benzodioxin-2-carboxylate A mixture of 20 g of the product A of Example 19, 200 ml of methanol and 6 ml of an ether-boron trifluoride complex was stirred at 20° C. for 16 hours and was then poured into a liter of aqueous saturated sodium chloride solution. The mixture was extracted with ether and the ether phase was washed with water until the wash water was neutral, dried over magnesium sulfate and evaporated to dryness under reduced pressure. The residue was chromatographed over silica gel and was eluted with petroleum ether (b.p.=60°–80° C.) containing 5% of ethyl acetate. The product was crystallized from methanol to obtain 3 g of isomer A of methyl 6-chloro-4-phenyl-4-(2-propenyl)-[4H]-1,3-benzodioxin-2-carboxylate melting at 70° C.

Analysis: $C_{19}H_{17}ClO_4$. Calculated: %C 66.18; %H 4.96; %Cl 10.28. Found: %C 66.1; %H 5.0; %Cl 10.5.

RMN Spectrum (deuterochloroform-60 MHz):

peaks at 155 to 200 Hz; 290 to 310 Hz and 323 to 380 Hz (hydrogens of propenyl); at 312 Hz (2-hydrogen); at 232 Hz (hydrogens of COOCH$_3$); at 412 to 443 (aromatic hydrogens).

EXAMPLE 21

6-chloro-4-ethenyl-4-phenyl-[4H]-1,3-benodioxin-2-carboxylic acid (mixture of 2 diastereoisomeric racemates)

STEP A: 5-chloro-2-hydroxy-α-phenyl-α-ethenyl-benzene-methanol 225 ml of a filtered solution of 2.5 M/liter of vinyl magnesium chloride in tetrahydrofuran were added dropwise with stirring at −10° C. to a mixture of 58 g of 5-chloro-2-hydroxy-benzophenone and 900 ml of anhydrous ether and the mixture was stirred at room temperature for 16 hours and was refluxed for 3 hours. The mixture was iced and 600 ml of aqueous 10% ammonium chloride solution and 50 ml of concentrated hydrochloric acid were added thereto dropwise. The decanted organic phase was washed twice with 100 ml of water, was dried over magnesium sulfate, filtered and evaporated to dryness under reduced pressure. The oil residue was chromatographed over silica gel and was eluted with methylene chloride to obtain 34.4 g of 5-chloro-2-hydroxy-α-phenyl-α-ethenyl-benzene-methanol.

Analysis: $C_{15}H_{13}ClO_2$. Calculated: %C 69.1; %H 5.02; %Cl 13.61; Found: %C 70.3; %H 5.0; %Cl 14.1.

STEP B: 6-chloro-4-phenyl-4-ethenyl-[4H]-1,3-benzodioxin-2-carboxylic acid (mixture of 2 diastereoisomeric racemates)

A mixture of 16 ml of dichloroacetic acid in 100 ml of dioxane was added with stirring over 30 minutes to a suspension of 24.6 g of sodium hydride as a 50% oil suspension, 1.6 g of dibenzo-18-courone-6 and 250 ml of anhydrous dioxane and then a solution of 33 g of the product of Step A in 150 ml of anhydrous dioxane was added thereto over one hour which progressively heating the mixture from 35° C. to 90° C. The mixture was stirred at 90° C. for 6 hours and was then cooled and poured into an ice-water mixture. The aqueous phase was washed 3 times with 500 ml of ether, was acidified with hydrochloric acid and was extracted three times with 500 ml of ether. The ether phase was extracted 3 times with 300 ml of an aqueous sodium bicarbonate solution and the aqueous phase was acidified with hydrochloric acid and was extracted 3 times with 300 ml of ether. The combined ether phases were washed with water until the wash water was neutral, dried over magnesium sulfate and evaporated to dryness under reduced pressure to obtain 38 g of raw 6-chloro-4-phenyl-4-ethenyl-[4H]-1,3-benzodioxin-2-carboxylic acid (mixture of 2 diastereoisomeric racemates).

RMN Spectrum (deuterochloroform-60 MHz):

peaks at 320 Hz (isomer A-2-hydrogen); at 345 Hz (isomer B-2-hydrogen); at 300 to 380 Hz (hydrogens of ethenyl); at 400 to 450 Hz (aromatic hydrogens).

EXAMPLE 22

Isomer A of methyl 6-chloro-4-phenyl-4-ethenyl-[4H]-1,3-benzodioxin-2-carboxylate A mixture of 38 g of the product of Example 21, 380 ml of methanol and 13.4 ml of ether-boron trifluoride complex was stirred at 20° C. for 16 hours and was then poured into a liter of aqueous saturated sodium chloride solution. The mixture was extracted 3 times with 400 ml of ether and the ether phase was washed with water until the wash water was neutral, dried over magnesium sulfate and evaporated to dryness under reduced pressure. The residue was pressure chromatographed over silica gel and was eluted with a 4-1 petroleum ether (b.p.=60°–80° C.)-ether mixture to obtain a fraction with an RF=0.25. The product was crystallized from 25 ml of methanol to obtain 6.2 g of isomer A of methyl 6-chloro-4-phenyl-4-ethenyl-[4H]-1,3-benzodioxin-2-carboxylate melting at 78° C.

Analysis: $C_{18}H_{15}ClO_4$. Calculated: %C 65.36; %H 4.57; %Cl 10.71. Found: %C 65.3; %H 4.6; %Cl 10.8.

RMN Spectrum (deuterochloroform-60 MHz):

peaks at 298 to 330 Hz; 363 to 374 Hz and 380 to 391 Hz (hydrogens of ethenyl); at 317 Hz (2-hydrogen); at 414 to 442 Hz (aromatic hydrogens); at 237 Hz (hydrogens of COOCH$_3$).

EXAMPLE 23

4,6-dimethyl-4-phenyl-[4H]-1,3-benzodioxin-2-carboxylic acid (mixture of 2 diastereoisomeric racemates)

STEP A: 5-methyl-2-hydroxy-α-methyl-α-phenyl-benzene-methanol 1000 ml of an ether solution titrating 0.51 M/liter of benzene magnesium bromide was added dropwise with stirring to an iced mixture of 38.5 g of 2-hydroxy-5-methyl-acetophenone in 100 ml of anhydrous ether and the mixture was stirred for 16 hours at room temperature and then heated at 40° C. for 2 hours. The solution was poured into a stirred mixture of 500 ml of ice and 250 ml of hydrochloric acid and the decanted organic phase was washed with water, dried over magnesium sulfate and evaporated to dryness under reduced pressure. The residue was crystallized from petroleum ether (b.p.=60°–80° C.) and then from cyclohexane to obtain 36.1 g of 5-methyl-2-hydroxy-α-methyl-α-phenyl-benzene-methanol melting at 100° C.

Analysis: $C_{23}H_{16}O_2$. Calculated: %C 78.9; %H 7.06. Found: %C 78.7; %H 7.1.

STEP B: 4,6-dimethyl-4-phenyl-[4H]-1,3-benzodioxin-2-carboxylic acid (mixture of 2 diastereoisomeric racemates)

A solution of 13 ml of dichloroacetic acid and 75 ml of dioxane was added over 40 minutes to a suspension of 1.6 g of dibenzo-18-courone-6, 20.2 g of sodium hydride as a 50% oil suspension and 250 ml of dioxane and then a solution of 30 g of the product of Step A in 150 ml of dioxane was added thereto at 60° C. over one hour. The mixture was heated at 90° C. for 2 hours, was cooled and poured into 500 ml of ice. The aqueous phase was washed 3 times with 300 ml of ether, was acidified with concentrated hydrochloric acid and was extracted 3 times with 300 ml of ether. The ether phase was extracted 4 times with 100 ml of aqueous sodium bicarbonate solution and the combined aqueous phase was acidified with hydrochloric acid and was extracted 3 times with 300 ml of ether. The ether phase was washed with water until the wash water was neutral, dried over magnesium sulfate and was evaporated to dryness under reduced pressure to obtain 28 g of raw 4,6-dimethyl-4-phenyl-[4H]-1,3-benzodioxin-2-carboxylic acid (mixture of 2 diastereoisomeric racemates).

RMN Spectrum (deuterochloroform-60 MHz):

peaks at 310 Hz (2-hydrogen-isomer A); at 340 Hz (2-hydrogenisomer B); at 405 to 450 Hz (aromatic hydrogens).

EXAMPLE 24

Isomer A of methyl 4,6-dimethyl-4-phenyl-[4H]-1,3-benzodioxin-2-carboxylate

A mixture of 28 g of the product of Example 23, 280 ml of methanol and 12.4 ml of boron trifluoride-ether complex was stirred at 20° C. for 16 hours and was then poured into 1000 ml of water. The mixture was extracted 3 times with 400 ml of ether and the combined ether phases were washed with water until the wash water was neutral, dried over magnesium sulfate and evaporated to dryness under reduced pressure. The residue was taken up in 110 ml of chloroform and 11.8 g of boron-trifluoride-ether complex and the mixture was stirred at 20° C. for 16 hours and was then poured into 1000 ml of an ice-water mixture. The mixture was extracted 4 times with 400 ml of ether and the ether phase was washed with water until the wash water was neutral, dried over magnesium sulfate and evaporated to dryness under reduced pressure to obtain 27.7 g of a mixture of A and B isomers. The product was pressure chromatographed over silica gel and was eluted with 1-4 ether-petroleum ether (b.p. = 60°-80° C.) mixture to recover a fraction with an Rf=0.35. The product was taken up in 30 ml of methanol to obtain 11 g of isomer A of methyl 4,6-dimethyl-4-phenyl-[4H]-1,3-benzodioxin-2-carboxylate melting at 100° C.

Analysis: $C_{18}H_{18}O_4$. Calculated: %C 72.46; %H 6.08. Found: %C 72.4; %H 6.2.

RMN Spectrum (deuterochloroform-90 MHz):

peaks at 465 Hz (2-hydrogen); at 345 Hz (hydrogens of COOCH$_3$); at 175 Hz (hydrogens of 4-CH$_3$); at 210 Hz (hydrogens of CH$_3$ on phenyl); at 617 to 668 Hz (aromatic hydrogens).

EXAMPLE 25

6-chloro-4-cyclohexyl-4-phenyl-[4H]-1,3-benzodioxin-2-carboxylic acid (mixture of 2 diastereoisomeric racemates)

STEP A: 5-chloro-2-hydroxy-α-cyclohexyl-α-phenyl-benzenemethanol 295 ml of an ether solution titrating 1.23 M/liter of cyclohexyl magnesium bromide were added over 2 hours at 40°-45° C. to a solution of 5-chloro-2-hydroxybenzophenone in 150 ml of anhydrous benzene and the ether was distilled while being replaced with benzene. The mixture was refluxed for 4 hours, was cooled and poured into a liter of ice and ammonium chloride. The mixture was extracted 3 times with 400 ml of ether and the combined ether phases were washed with water, dried over magnesium sulfate and evaporated to dryness under reduced pressure. The residue was taken up in 250 ml of cyclohexane to obtain 15.9 g of 5-chloro-2-hydroxy-α-cyclohexyl-α-phenyl-benzene-methanol melting at 170° C.

Analysis: $C_{19}H_{21}ClO_2$. Calculated: %C 72.02; %H 6.68; %Cl 11.18. Found: %C 71.7; %H 6.7; %Cl 11.5.

STEP B: 6-chloro-4-cyclohexyl-4-phenyl-[4H]-1,3-benzodioxin-2-carboxylic acid (mixture of 2 diastereoisomeric racemates)

A mixture of 5 ml of dichloroacetic acid and 35 ml of dioxane was added over 25 minutes at 20°-35° C. to a suspension of 0.5 g of dibenzo-18-courone-6, 8.9 g of sodium hydride as a 50% oil suspension and 92 ml of dioxane and the mixture was heated to 50° C. A solution of 15.4 g of the product of Step A in 100 ml of dioxane was added thereto over 45 minutes while progressively heating to 90° C. and the mixture was stirred at 90° C. for 4 hours, was cooled and was poured into 800 ml of ice. The aqueous phase was washed 3 times with 200 ml of ether, was acidified with concentrated hydrochloric acid and was extracted 3 times with 250 ml of ether. The ether phase was extracted 4 times with 200 ml of aqueous sodium bicarbonate solution and the combined aqueous phases were acidified with hydrochloric acid and were extracted 3 times with 300 ml of ether. The ether phase was washed with water until the wash water was neutral, dried over magnesium sulfate and evaporated to dryness under reduced pressure to obtain 8.6 g of raw 6-chloro-4-cyclohexyl-4-phenyl-[4H]-1,3-benzodioxin-2-carboxylic acid (mixture of 2 diatereoisomeric racemates).

RMN Spectrum (deuterochloroform-60 MHz):

peaks at 323 Hz (2-hydrogen-isomer A); at 333 Hz (2-hydrogenisomer B); at 410 to 460 Hz (aromatic hydrogens); at 55 to 105 Hz (hydrogens of cyclohexyl).

EXAMPLE 26

Isomer A of methyl 6-chloro-4-cyclohexyl-4-phenyl-[4H]-1,3-benzodioxin-2-carboxylate A mixture of 8.6 g of the product of Example 25, 90 ml of methanol and 2.9 ml of ether-boron trifluoride complex was stirred for 16 hours and was then poured into 500 ml of water. The mixture was extracted with ether and the organic phase was washed twice with 100 ml of water, then with an aqueous sodium bicarbonate solution, then with water, dried over magnesium sulfate and evaporated to dryness under reduced pressure to obtain 6.2 g of product in the form of A and B isomers. 4 g of the said product in 3.5 ml of methylene chloride and 1.3 g of ether-boron trifluoride complex was stirred at 20° C. for 48 hours and was then poured into 100 ml of water. The mixture was extracted with 3 times with 20 ml of methylene chloride and the organic phase was washed with water, dried over magnesium sulfate and evaporated to dryness under reduced pressure to obtain 2.65 g of product which was crystallized from 100 ml of methanol to obtain 1.6 g of isomer A of methyl 6-chloro-4-cyclohexyl-4-phenyl-[4H]-1,3-benzodioxin-2-carboxylate melting at 142° C.

Analysis: $C_{22}H_{23}ClO_4$. Calculated: %C 68.30; %H 5.99; %Cl 9.16. Found: %C 68.1; %H 6.1; %Cl 9.5.

RMN Spectrum (deuterochloroform-60 MHz): peaks at 319 Hz (2-hydrogen); at 234 Hz (hydrogens of $COOCH_3$); at 55 to 135 Hz (hydrogens of cyclohexyl); at 410 to 455 Hz (aromatic hydrogens).

EXAMPLE 27

6-cyclohexyl-4-methyl-4-phenyl-[4-H]-1,3-benzodioxin-2-carboxylic acid (mixture of 2 diastereoisomeric racemates)

STEP A: 1-(2-hydroxy-5-cyclohexyl-phenyl)-ethanone 35.25 g of 4-cyclohexyl-phenol were added in small amounts at 5° to 10° C. to a solution of 46 g of boron trifluoride in 110 ml of concentrated acetic acid and the mixture was held at 50° C. for 15 minutes and then at 75° C. for 21 hours. The mixture was poured into ice and the aqueous phase was extracted 3 times with 200 ml of ether. The ether phase was treated with powdered sodium bicarbonate and was stirred for 16 hours and was then filtered. The filtrate was washed with water until the wash water was neutral, dried over magnesium sulfate and was evaporated to dryness under reduced pressure. The residue was pressure chromatographed over silica gel and was eluted with a 1-4 ether-petroleum ether (b.p.=60° to 80° C.) mixture to obtain 39.9 g of 1-(2-hydroxy-5-cyclohexylphenyl)-ethanone melting at <50° C.

Analysis: $C_{14}H_{18}O_2$. Calculated: %C 77.03; %H 8.31. Found: %C 77.3; %H 8.4.

STEP B: 5-cyclohexyl-2-hydroxy-α-methyl-α-phenyl-benzenemethanol 310 ml of an ether solution titrating 0.76 M/liter of phenyl magnesium bromide were added over 1 hour to a mixture of 23.4 g of the product of Step A and 230 ml of anhydrous ether and the mixture was stirred for 16 hours at room temperature and was poured over ice. The mixture was acidified with 200 ml of 2 N hydrochloric acid and was extracted 3 times with 250 ml of ether. The organic phase was washed 3 times with 100 ml of water, dried over magnesium sulfate and evaporated to dryness under reduced pressure. The residue was taken up in 120 ml of petroleum ether (b.p.=60° to 80° C.) and the mixture was vacuum filtered. The product was dried to obtain 22.55 g of 5-cyclohexyl-2-hydroxy-α-methyl-α-phenyl-benzene-methanol melting at 119° C.

Analysis: $C_{14}H_{18}O_2$. Calculated: %C 81.04; %H 8.16. Found: %C 81.0; %H 8.1.

STEP C: 6-cyclohexyl-4-methyl-4-phenyl-[4H]-1,3-benzodioxin-2-carboxylic acid (mixture of 2-diastereoisomeric racemates)

A solution of 14.18 g of dichloroacetic acid in 150 ml of dioxane was added with stirring at room temperature to a mixture of 11.8 g of sodium hydride as a 50% oil suspension, 120 ml of dioxane and 1.05 g of dibenzo-18-courone-6 and then a solution of 20.74 g of the product of Step B in 250 ml of dioxane was added dropwise thereto. The mixture was stirred at 80° C. for 2 hours and was cooled and poured into ice. The aqueous phase was washed with 300 ml of ether, was acidified with 30 ml of concentrated hydrochloric acid and was extracted 3 times with 250 ml of ether. The ether phase was washed twice with 100 ml of water and was extracted twice with 250 ml of aqueous 5% sodium bicarbonate solution. The aqueous phase was washed with 100 ml of ether, acidified with 60 ml of concentrated hydrochloric acid and was extracted 3 times with 250 ml of ether. The decanted organic phase was washed with water until the wash water was neutral, dried over magnesium sulfate and was evaporated to dryness under reduced pressure to obtain 18.7 g of raw 6-cyclohexyl-4-methyl-4-phenyl-[4H]-1,3-benzodioxin-2-carboxylic acid (mixture of 2 diastereoisomeric racemates).

RMN Spectrum (deuterochloroform-60 MHz): peaks at 116.5 Hz (2-hydrogen-isomer A); at 125.5 Hz (2-hydrogen-isomer B); at 311 Hz (Hydrogens of 4-$CH_3$-isomer A); at 347 Hz (hydrogens of 4-$CH_3$-isomer B).

EXAMPLE 28

Isomer A of methyl 6-cyclohexyl-4-methyl-4-phenyl-[4H]-1,3-benzodioxin-2-carboxylate 7.52 g of ether-boron trifluoride were added dropwise at 15° C. to a mixture of 18.7 g of the product of Example 27 and 190 ml of methylene chloride and the mixture was stirred for 2 hours at room temperature. 190 ml of methanol were added thereto and was then stirred at room temperature for 24 hours and was poured into 500 ml of aqueous saturated sodium chloride solution. The mixture was extracted 3 times with 200 ml of methylene chloride and the organic phase was washed twice with 500 ml of aqueous 5% sodium bicarbonate solution and twice with 75 ml of water until neutral, dried over magnesium sulfate and evaporated to dryness under reduced pressure. The residue was pressure chromatographed over silica gel and was eluted with a 1-4 ether-petroleum ether (b.p.=60°-80° C.) mixture to obtain 4 g of isomer A of methyl 6-cyclohexyl-4-methyl-4-phenyl-[4H]-1,3-benzodioxin-2-carboxylate melting at 107° C.

Analysis: $C_{23}H_{26}O_4$. Calculated: %C 75.38; %H 7.15. Found: %C 75.4; %H 7.1.

RMN Spectrum (deuterochloroform-60 MHz): peaks at 116 Hz (hydrogens of 4-$CH_3$); at 230.5 Hz (hydrogens of $COOCH_3$); at 310 Hz (2-hydrogen); at 65 to 125 Hz (hydrogens of cyclohexyl); at 410 to 450 Hz (aromatic hydrogens).

EXAMPLE 29

6-methoxy-4-methyl-4-phenyl-[4H]-1,3-benzodioxin-2-carboxylic acid (mixture of 2 diastereoisomeric racemates)

STEP A: 5-methoxy-2-hydroxy-α-methyl-α-phenyl-benzenemethanol 500 ml of an ether solution titrating 0.55 M/liter of phenyl magnesium bromide were added dropwise with stirring to an iced solution of 20.5 g of 2-hydroxy-5-methoxy-acetophenone in ether and the mixture was stirred for 16 hours at room temperature and was then poured into 500 ml of ice and 100 ml of concentrated hydrochloric acid. The decanted ether phase was washed with water, dried over magnesium sulfate and evaporated to dryness under reduced pressure. The residue was taken up in 100 ml of petroleum ether (b.p.=60°–80° C.) and the mixture was vacuum filtered to obtain 28.3 g of raw 5-methoxy-2-hydroxy-α-methyl-α-phenyl-benzene-methanol melting at 114° C.

Analysis: $C_{15}H_{16}O_3$. Calculated: %C 73.75; %H 6.6. Found: %C 73.8; %H 6.7.

STEP B: 6-methoxy-4-methyl-4-phenyl-[4H]-1,3-benzodioxin-2-carboxylic acid (mixture of 2 diastereoisomeric racemates)

A solution of 17 g of dichloroacetic acid in 180 ml of dioxane was added dropwise with stirring to a suspension of 14.9 g of sodium hydride as 50% oil suspension, 1.1 g of dibenzo-18-courone-6 and 160 ml of dioxane and then a solution of 21.5 g of the product of Step A in 220 ml of dioxane was added. The reaction mixture was heated at 90° C. for 3 hours, was cooled and was poured into ice. The aqueous phase was washed with 300 ml of ether, was acidified with 30 ml of concentrated hydrochloric acid and was extracted 3 times with 200 ml of ether. The ether phase was washed twice with 100 ml of water and was extracted twice with 250 ml of aqueous 5% sodium bicarbonate solution. The aqueous phase was washed with 100 ml of ether, acidified with 40 ml of concentrated hydrochloric acid and was extracted 3 times with 250 ml of ether. The combined organic phases were washed with water until the water was neutral, dried over magnesium sulfate and evaporated under reduced pressure to obtain 29.8 g of raw 6-methoxy-4-methyl-4-phenyl-[4H]-1,3-benzodioxin-2-carboxylic acid (mixture of 2 diastereoisomeric racemates).

RMN Spectrum (deuterochloroform-60 MHz):
peaks at 310 Hz (2-hydrogen-A isomer); at 340 Hz (2-hydrogen-B isomer); at 117 Hz (hydrogens of 4-$CH_3$-isomer A); at 125 Hz (hydrogens of 4-$CH_3$-isomer B).

EXAMPLE 30

Isomer A of methyl 6-methoxy-4-methyl-4-phenyl-[4H]-1,3-benzodioxin-2-carboxylate A mixture of 29.8 g of the product of Example 29, 300 ml of methanol and 12.5 ml of an ether-boron trifluoride complex was stirred at room temperature for 36 hours and was poured into 500 ml of an aqueous saturated sodium chloride solution. The mixture was extracted 3 times with 200 ml of ether and the ether phase was washed twice with 50 ml of an aqueous 50% sodium bicarbonate solution. The decanted combined organic phases were washed twice with 50 ml of water until the wash water was neutral, dried over magnesium sulfate and was evaporated to dryness under reduced pressure to obtain 26.3 g of a mixture of A and B isomers. The latter was taken up in 275 ml of methylene chloride and 10.6 ml of boron trifluoride-ether complex and the mixture was stirred for 16 hours at room temperature and was poured into ice. The decanted organic phase was washed twice with 50 ml of an aqueous 5% sodium bicarbonate solution and then with water until the wash water was neutral, dried over magnesium sulfate and evaporated to dryness under reduced pressure. The residue was pressure chromatographed over silica gel and was eluted with a 1-4 ether-petroleum ether (b.p.=60°–80° C.) mixture to obtain a first fraction which was crystallized from 12 ml of methanol to obtain 3.75 g of isomer A of methyl 6-methoxy-4-methyl-4-phenyl-[4H]-1,3-benzodioxin-2-carboxylate and a second fraction which was crystallized from 7 ml of methanol to obtain 1.6 g of the isomer A for a total yield of 5.35 g melting at 70°–71° C.

Analysis: $C_{18}H_{18}O_5$. Calculated: %C 68.78; %H 5.77. Found: %C 68.5; %H 5.7; %C 68.8; %H 5.8.

RMN Spectrum (deuterochloroform-60 MHz):
1st fraction—peaks at 116 Hz (hydrogens of 4-$CH_3$); at 227.5 and 229.5 Hz (hydrogens of $COOCH_3$ and $OCH_3$); at 308.5 Hz (2-hydrogen); at 402 to 418 Hz and 434 to 450 Hz (aromatic hydrogens).

2nd fraction—peaks at 117 Hz (hydrogens of 4-$CH_3$); at 229 and 232 Hz (hydrogens of $COOCH_3$ and $OCH_3$); at 313.5 Hz (2-hydrogen); at 409 to 421 Hz and 440 to 450 Hz (aromatic hydrogens).

EXAMPLE 31

6-chloro-4-phenyl-4-benzyl-[4H]-1,3-benzodioxin-2-carboxylic acid (mixture of 2 diastereoisomeric racemates)

STEP A: 5-chloro-2-hydroxy-α-benzyl-α-phenyl-benzenemethanol 322 ml of an ether solution titrating 1.12 M/liter of benzyl magnesium chloride were added over one hour to a solution of 34 g of 5-chloro-2-hydroxy-benzophenone in 150 ml of benzene and the mixture was allowed to stand for one hour and was then stirred at 20° C. for 16 hours. The mixture was poured into one liter of aqueous saturated ammonium chloride solution and the mixture was washed with water and was extracted 3 times with 400 ml of ether. The ether phase was dried over magnesium sulfate and was evaporated to dryness under reduced pressure. The residue was taken up in 100 ml of cyclohexane and the mixture stood for 16 hours at 20° C. and was iced and vacuum filtered to obtain 42.9 g of 5-chloro-2-hydroxy-α-benzyl-α-phenyl-benzene methanol melting at 128° C.

RMN Spectrum (deuterochloroform-60 MHz):
peaks at 500 Hz (hydrogen of 2-OH); at 180 Hz (hydrogen of α-OH); at 215 Hz (hydrogens of α-$CH_2$); at 395–440 Hz (aromatic hydrogens).

STEP B: 6-chloro-4-phenyl-4-benzyl-[4H]-1,3-benzodioxin-2-carboxylic acid (mixture of 2 diastereoisomeric racemates)

A solution of 9.9 ml of dichloroacetic acid in 70 ml of dioxane was added over 40 minutes at 20° to 45° C. to a suspension of 1.6 g of dibenzo-18-courone-6, 16.8 g of sodium hydride as a 50% oil suspension and 250 ml of dioxane and a solution of the product of Step A in 150 ml of dioxane was added thereto over 45 minutes at 90° C. The mixture was heated at 90° C. for 6 hours and was then stirred at 20° C. for 16 hours and was poured into one liter of ice. The aqueous phase was washed twice with 300 ml of ether, was acidified with hydrochloric acid and was extracted 3 times with 400 ml of ether. The ether phase was extracted 4 times with 150 ml of an aqueous sodium bicarbonate solution and the aqueous phase was acidified with hydrochloric acid and was extracted 3 times with 300 ml of ether. The ether phase was washed with water until the wash water was neutral, dried over magnesium sulfate and evaporated to dryness under reduced pressure to obtain 31.5 g of raw 6-chloro-4-phenyl-4-benzyl-4H]-1,3-benzodioxin-2-carboxylic acid (mixture of 2 diastereoisomeric racemates).

RMN Spectrum (deuterochloroform-60 MHz):
peaks at 312 Hz (2-hydrogen); at 190 to 225 Hz (hydrogens of 4-$CH_2$); at 400 to 460 Hz (aromatic hydrogens).

EXAMPLE 32

Isomer A of methyl 6-chloro-4-phenyl-4-benzyl-[4H]-1,3-benzodioxin-2-carboxylate A mixture of 31.5 g of the product of Example 31, 300 ml of methanol and 10.5 ml of ether-boron trifluoride complex was stirred for 16 hours at 20° C. and was poured into one liter of water. The mixture was extracted 3 times with 400 ml of ether and the ether phase was washed with an aqueous sodium bicarbonate solution and twice with 200 ml of water, dried over magnesium sulfate and evaporated to dryness under reduced pressure. The residue was taken up in 75 ml of methylene chloride and 8.2 ml of ether-boron trifluoride complex and the mixture was stirred at 20° C. for 16 hours and was poured into 100 ml of water. The aqueous phase was extracted 3 times with 50 ml of methylene chloride and the organic phase was washed with water until the wash water was neutral, dried over magnesium sulfate and evaporated to dryness under reduced pressure. The residue was crystallized from 120 ml of methanol to obtain 12 g of isomer A of methyl 6-chloro-4-phenyl-4-benzyl-[4H]-1,3-benzodioxin-2-carboxylate melting at 110° C.

Analysis: $C_{23}H_{19}ClO_4$. Calculated: %C 69.96; %H 4.85; %Cl 8.97. Found: %C 69.6; %H 4.8; %Cl 9.0.

RMN Spectrum (deuterochloroform-60 MHz):
peaks at 232 Hz (hydrogens of $COOCH_3$); at 188 to 203 Hz and 213 to 218 Hz (hydrogens of 4-$CH_2$); at 405–450 Hz (aromatic hydrogens).

EXAMPLE 33

6-(4-chlorophenoxy)-4-methyl-4-phenyl-[4H]-1,3-benzodioxin-2-carboxylic acid (mixture of 2 diastereoisomeric racemates)

STEP A: 2-hydroxy-5-(4-chlorophenoxy)-acetophenone

A mixture of 2 g of 4-(4-chlorophenoxy)-phenol and 6 ml of boron trifluoride in acetic acid was stirred at 90° C. for 72 hours and was then poured into 25 ml of water. The mixture was extracted 3 times with 25 ml of ether and the ether phase was washed with water, aqueous sodium bicarbonate solution and water until the wash water was neutral, dried over magnesium sulfate and evaporated to dryness under reduced pressure. The residue was taken up in heptane to obtain 1.7 g of 2-hydroxy-5-(4-chlorophenoxy)-acetophenone melting at 88° C.

Analysis: $C_{14}H_{11}ClO_3$. Calculated: %C 64.01; %H 4.22; %Cl 13.5. Found: %C 63.9; %H 4.4; %Cl 13.3.

STEP B: 5-(4-chlorophenoxy)-2-hydroxy-α-methyl-α-phenylbenzene-methanol 210 ml of an ether solution titrating 0.8 M/liter of phenyl magnesium bromide were added dropwise at 10° to 20° C. to a solution of 20 g of the product of Step A in 400 ml of ether cooled in an ice bath and the solution was stirred for 16 hours at room temperature and was then poured into 200 g of ice containing 20 to 30 ml of concentrated hydrochloric acid. The organic phase was washed with water, with aqueous sodium bicarbonate solution, with water, dried over magnesium sulfate and treated with activated carbon and was filtered. The filtrate was evaporated to dryness and the residue was taken up in 200 ml of boiling cyclohexane. The mixture was cooled and was held at 10° C. for one hour and was filtered. The product was empasted with hexane and was dried at 60° C. to obtain 21.05 g of 5-(4-chlorophenoxy)-2-hydroxy-α-methyl-α-phenyl-benzene-methanol melting at 103°–104° C.

Analysis: $C_{20}H_{17}ClO_3$. Calculated: %C 70.48; %H 5.03; %Cl 10.4. Found: %C 70.4; %H 5.1; %Cl 10.2.

STEP C: 6-(4-chlorophenoxy)-4-methyl-4-phenyl-[4H]-1,3-benzodioxin-2-carboxylic acid (mixture of 2 diastereoisomeric racemates)

A solution of 5.7 ml of dichloroacetic acid and 50 ml of dioxane was added over 30 minutes at 22° to 42° C. to a mixture of 1 g of dibenzo-18-courone-6, 8.9 g of sodium hydride as a 50% oil suspension and 125 ml of dioxane and then a solution of 20 g of the product of Step B in 80 ml of dioxane was added thereto at 40° to 90° C. over 45 minutes. The mixture was refluxed for 6 hours, was cooled and poured into 500 ml of ice. The aqueous phase was washed 3 times with 200 ml of ether, was acidified with hydrochloric acid and was extracted 3 times with 200 ml of ether. The ether phase was extracted with an aqueous sodium bicarbonate solution and the aqueous phase was acidified with hydrochloric acid. The aqueous phase was extracted 3 times with 250 ml of ether and the ether phase was washed with water until the wash water was neutral, dried over magnesium sulfate and evaporated to dryness under reduced pressure to obtain 27 g of raw 6-(4-chlorophenoxy)-4-methyl-4-phenyl-[4H]-1,3-benzodioxin-2-carboxylic acid (mixture of 2 diastereoisomeric racemates).

RMN Spectrum (deuterochloroform-60 MHz):
peaks at 116 Hz (hydrogens of 4-$CH_3$-isomer A); at 126 Hz (hydrogens of 4-$CH_3$-isomer B); at 316 Hz (2-hydrogen-isomer A); at 346 Hz (2-hydrogen-isomer B).

EXAMPLE 34

Isomer A of methyl 6-(4-chlorophenoxy)-4-methyl-4-phenyl-[4H]-1,3-benzodioxin-2-carboxylate 7.4 ml of boron trifluoride-ether complex were added at 0° C. to a solution of 23 g of the product of Example 33 in 100 ml of methylene chloride and the mixture stood at room temperature for 90 minutes. 200 ml of methanol were added thereto and the mixture was stirred at 20° C. for 16 hours and was then poured into 600 ml of aqueous sodium chloride solution. The mixture was extracted 3 times with 200 ml of methylene chloride and the organic phase was washed 3 times with 200 ml of water, twice with 100 ml of aqueous sodium bicarbonate solution and then twice with 200 ml of water, dried over magnesium sulfate and evaporated to dryness under reduced pressure to obtain 21 g of a mixture of A and B isomers. The latter was chromatographed over silica gel and was eluted with a 1–4 ether-petroleum ether (b.p.=60° to 80° C.) mixture to obtain a fraction with an Rf=0.18. The product was crystallized from 30 ml of methanol to obtain 8.8 g of isomer A of methyl 6-(4-chlorophenoxy)-4-methyl-4-phenyl-[4H]-1,3-benzodioxin-2-carboxylate melting at 100° C.

Analysis: $C_{23}H_{19}ClO_5$. Calculated: %C 67.24; %H 4.66; %Cl 8.62. Found: %C 67.3; %H 4.7; %Cl 8.9.

RMN Spectrum (deuterochloroform-60 MHz):
peaks at 114.5 Hz (hydrogens of 4-$CH_3$); at 312 Hz (2-hydrogen); at 231 Hz (hydrogens of $COOCH_3$); at 410 to 441 Hz (aromatic hydrogens).

EXAMPLE 35

Tablets were prepared containing either 300 mg of 6-chloro-4,4-dimethyl-[4H]-1,3-benzodioxin-2-carboxylic acid or 200 mg of isomer A of methyl 6-chloro-4-methyl-4-(3-trifluoromethylphenyl)-[4H]-1,3-benzodioxin-2-carboxylate and sufficient excipient of lactose, starch, talc and magnesium stearate for a final weight of 500 mg. Gelules were prepared containing either 300 mg of [4H]-1,3-benzodioxin-2-carboxylic acid or 250 mg of isomer A of methyl 6-chloro-4-ethenyl-4-phenyl-[4H]-1,3-benzodioxin-2-carboxylate and sufficient excipient of talc aerosil and magnesium stearate for a final weight of 500 mg.

PHARMACOLOGICAL DATA

A. Hypolipemiant Activity

This test was effected on groups of 8 male rats of the Sprague Dawley S.P.F. strain weighing about 200 g and the animals received a regime containing 50% of saccharose and which was rich in cholesterol (1%). The rats were treated over 10 days with the test products which were administered through an esophagus tube as a suspension in water containing carboxymethylcellulose. The animals were left without food 16 hours after the last administration of the test product and then killed by an abdominal puncture and from the blood sample with sodium heparinate, the levels of triglycerides, cholesterol and total lipids were determined by the following methods.

The triglyceride level was determined by the semiautomatic technique of Kessler et al [Automation in Analytical Chemistry, 1965, p. 341] modified by Claude et al [Ann. Biol. Clin., Vol. 26 3-4 (1968), p. 451]. The cholesterol levels were determined by the technique of Levine [Symposium Technicon, Vol. I, (1967), p. 25] adapted to auto-analyzer system I. The nephelometric level of total lipids was determined semi-automatically by the method of Girard et al. [Symposium Technicon, 1970]. The variations expressed in percentages of the level of triglycerides, cholesterol and total lipids after administration of the various dosage of the test products in the treated animals as compared to the untreated controls and the results are reported in Table I.

TABLE I

| Product of Example | Doses in mg/kg day | % Variation of levels | | |
|---|---|---|---|---|
| | | Triglycerides | Cholesterol | Total Lipids |
| 1 | 50 | −11 | −37 | −39 |
| 2 | 50 | −11 | −23 | −28 |
| 18 | 5 | −47 | −41 | −51 |
| 18 | 2 | −15 | −30 | −29 |
| 22 | 5 | −79 | −35 | −34 |
| 30 | 5 | −33 | −43 | −41 |
| 32 | 5 | −11 | −45 | −41 |

B. Acute Toxicity

The acute toxicity was determined on groups of 5 mice weighing about 18 to 22 g and the test products were intraperitoneally administered in suspension in an aqueous carboxymethylcellulose. The mice were observed for one week and $DL_{50}$ dose was determined as reported in Table II.

TABLE II

| Product of Example | $DL_{50}$ in mg/kg |
|---|---|
| 1 | 200 |
| 2 | 450 |
| 18 | >1000 |
| 22 | ≈700 |
| 30 | >1000 |
| 32 | >1000 |

Various modifications of the products and process of the invention may be made without departing from the spirit or scope thereof and it should be understood that the invention is intended to be limited only as defined in the appended claims.

We claim:

1. A compound selected from the group consisting of racemates and optically active isomers and mixtures of isomers of a compound of the formula

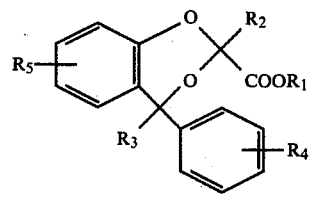

wherein $R_1$ is selected from the group consisting of hydrogen, alkyl of 1 to 5 carbon atoms, alkali metal, alkaline earth metal, aluminum, $-NH_4$ and non-toxic, pharmaceutically acceptable organic amines, $R_2$ is selected from the group consisting of hydrogen and alkyl of 1 to 5 carbon atoms, $R_4$ and $R_5$ are individually selected from the group consisting of hydrogen, halogen, trifluoromethyl, cyclohexyl, alkyl and alkoxy of 1 to 3 carbon atoms and p-chlorophenoxy and $R_3$ is selected from the group consisting of 2-propenyl, ethenyl, cyclohexyl, benzyl, alkyl of 1 to 5 carbon atoms and hydrogen with the proviso that when $R_3$ is alkyl, at least one of $R_4$ and $R_5$ is not hydrogen or halogen and when $R_3$ is hydrogen, at least one of $R_4$ and $R_5$ is not hydrogen, halogen or trifluoromethyl.

2. A compound of claim 1 wherein $R_1$ and $R_2$ are individually selected from the group consisting of hydrogen and methyl, $R_4$ and $R_5$ are individually selected from the group consisting of hydrogen, chlorine, $-CF_3$, cyclohexyl, methoxy, methyl and p-chlorophenoxy and $R_3$ is selected from the group consisting of 2-propenyl, ethenyl, cyclohexyl, benzyl and methyl with the proviso that when $R_3$ is methyl, at least one of $R_4$ and $R_5$ is not hydrogen or chlorine.

3. A compound of claim 1 wherein $R_1$ and $R_2$ are individually selected from the group consisting of hydrogen and methyl, $R_4$ is hydrogen or $-CF_3$, $R_5$ is selected from the group consisting of hydrogen, chlorine, $-CF_3$, cyclohexyl, methoxy and p-chlorophenoxy, $R_3$ is selected from the group consisting of 2-propenyl, ethenyl, cyclohexyl, benzyl and methyl with the proviso that when $R_3$ is methyl, at least one of $R_4$ and $R_5$ is not hydrogen or chlorine.

4. A compound of claim 1 selected from the group consisting of racemates and optically active isomers of methyl 6-chloro-4-methyl-4-(3-trifluoromethylphenyl)-[4H]-1,3-benzodioxin-2-carboxylate and methyl 6-methoxy-4-methyl-4-phenyl-[4H]-1,3-benzodioxin-2-carboxylate and methyl 6-chloro-4-phenyl-4-benzyl-[4H]-1,3-benzodioxin-2-carboxylate.

5. A compound of claim 1 which is the A isomer of methyl 6-chloro-4-methyl-4-(3-trifluoromethylphenyl)-[4H]-1,3-benzodioxin-2-carboxylate.

6. An hypolipemiant composition comprising an hypolipemiantly effective amount of at least one compound of claim 1 and an excipient.

7. A composition of claim 6 wherein $R_1$ and $R_2$ are individually selected from the group consisting of hydrogen and methyl, $R_4$ and $R_5$ are individually selected from the group consisting of hydrogen, chlorine, —$CF_3$, cyclohexyl methoxy, methyl and p-chlorophenoxy and $R_3$ is selected from the group consisting of 2-propenyl, ethenyl, cyclohexyl, benzyl and methyl with the proviso that when $R_3$ is methyl, at least one of $R_4$ and $R_5$ is not hydrogen or chlorine.

8. A composition of claim 6 wherein $R_1$ and $R_2$ are individually selected from the group consisting of hydrogen and methyl, $R_4$ is hydrogen or —$CF_3$, $R_5$ is selected from the group consisting of hydrogen, chlorine, —$CF_3$, cyclohexyl, methoxy and p-chlorophenoxy, $R_3$ is selected from the group consisting of 2-propen-1, ethenyl, cyclohexyl, benzyl and methyl with the proviso that when $R_3$ is methyl, at least one of $R_4$ and $R_5$ is not hydrogen or chlorine.

9. A composition of claim 6 selected from the group consisting of racemates and optically active isomers of methyl 6-chloro-4-methyl-4-(3-trifluoromethylphenyl)-[4H]-1,3-benzodioxin-2-carboxylate and methyl 6-methoxy-4-methyl-4-phenyl-[4H]-1,3-benzodioxin-2-carboxylate and methyl 6-chloro-4-phenyl-4-benzyl-[4H]-1,3-benzodioxin-2-carboxylate.

10. A composition of claim 6 which is the A isomer of methyl 6-chloro-4-methyl-4-(3-trifluoromethylphenyl)-[4H]-1,3-benzodioxin-2-carboxylate.

11. A method of inducing hypolipemic activity in warm-blooded animals comprising administering to warm-blooded animals an hypolipemiantly effective amount of at least one compound of racemates and optically active isomers and mixtures of isomers of a [4H]-1,3-benzodioxin-2-carboxylic acid compound of claim 1.

12. The method of claim 11 wherein $R_1$ and $R_2$ are individually selected from the group consisting of hydrogen and methyl, $R_4$ and $R_5$ are individually selected from the group consisting of hydrogen, chlorine, —$CF_3$, cyclohexyl, methoxy, methyl and p-chlorophenoxy and $R_3$ is selected from the group consisting of 2-propenyl, ethenyl, cyclohexyl, benzyl and methyl with the proviso that when $R_3$ is methyl, at least one of $R_4$ and $R_5$ is not hydrogen or chlorine.

13. The method of claim 11 wherein $R_1$ and $R_2$ are individually selected from the group consisting of hydrogen and methyl, $R_4$ is hydrogen or —$CF_3$, $R_5$ is selected from the group consisting of hydrogen, chlorine, —$CF_3$, cyclohexyl, methoxy and p-chlorophenoxy, $R_3$ is selected from the group consisting of 2-propenyl, ethenyl, cyclohexyl, benzyl and methyl with the proviso that when $R_3$ is methyl, at least one of $R_4$ and $R_5$ is not hydrogen or chlorine.

14. The method of claim 11 selected from the group consisting of racemates and optically active isomers of methyl 6-chloro-4-methyl-4-(3-trifluoromethylphenyl)-[4H]-1,3-benzodioxin-2-carboxylate and methyl 6-methoxy-4-methyl-4-phenyl-[4H]-1,3-benzodioxin-2-carboxylate and methyl 6-chloro-4-phenyl-4-benzyl-[4H]-1,3-benzodioxin-2-carboxylate.

15. The method of claim 11 which is the A isomer of methyl 6-chloro-4-methyl-4-(3-trifluoromethylphenyl)-[4H]-1,3-benzodioxin-2-carboxylate.

* * * * *

UNITED STATES PATENT AND TRADEMARK OFFICE
CERTIFICATE OF CORRECTION

PATENT NO. : 4,281,012
DATED : July 28, 1981
INVENTOR(S) : DANIEL HUMBERT ET AL.

It is certified that error appears in the above—identified patent and that said Letters Patent is hereby corrected as shown below:

Preamble page, [57] Abstract second column, line 7 from bottom: "no" should read -- not --.

Column 18, line 51: "% Cl 12.9" second occurrence, should read -- % Cl 13.1 --.

Signed and Sealed this

Eighth Day of December 1981

[SEAL]

Attest:

*Attesting Officer*

GERALD J. MOSSINGHOFF
*Commissioner of Patents and Trademarks*